(12) United States Patent
Morrison et al.

(10) Patent No.: US 9,943,641 B2
(45) Date of Patent: Apr. 17, 2018

(54) PACKAGE FOR MEDICAL PRODUCT

(71) Applicant: Becton, Dickinson and Company, Franklin Lakes, NJ (US)

(72) Inventors: Matthew Morrison, Morristown, NJ (US); Joshua David Horvath, San Ramon, CA (US); James Sullivan, West Boylston, MA (US); Stephen Lynn Richards, Careywood, ID (US); Victor Politis, Natick, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 158 days.

(21) Appl. No.: 13/830,009

(22) Filed: Mar. 14, 2013

(65) Prior Publication Data

US 2014/0262923 A1    Sep. 18, 2014

(51) Int. Cl.
*A61M 5/00* (2006.01)
*A61M 5/158* (2006.01)

(52) U.S. Cl.
CPC ..... *A61M 5/002* (2013.01); *A61M 2005/1585* (2013.01)

(58) Field of Classification Search
CPC ....... B65D 77/2024; B65B 3/022; B65B 9/04; A61M 5/002; A61M 2005/1585
USPC .............. 206/438, 439, 570, 571, 370, 363; 53/452, 453
See application file for complete search history.

(56) References Cited

U.S. PATENT DOCUMENTS

| | | | |
|---|---|---|---|
| 2,966,986 A | 1/1961 | Jones | |
| 3,013,656 A * | 12/1961 | Murphy, Jr. .......... | A61J 7/0069 206/223 |
| 3,247,851 A | 4/1966 | Seibert | |
| D218,403 S | 8/1970 | Friedberg | |
| 3,730,338 A * | 5/1973 | Chesky ................. | A61B 42/40 206/278 |
| 3,825,002 A | 7/1974 | Paige | |
| 3,851,649 A * | 12/1974 | Villari ................ | A61M 25/002 206/223 |
| 4,153,160 A * | 5/1979 | Leigh .................... | A61B 50/33 206/370 |
| D260,368 S | 8/1981 | Dunshee et al. | |
| 4,469,226 A | 9/1984 | Matney | |

(Continued)

FOREIGN PATENT DOCUMENTS

| | | |
|---|---|---|
| EP | 0916355 | 5/1999 |
| EP | 2201976 | 6/2010 |

(Continued)

OTHER PUBLICATIONS

Comfort Infusion Set, Photographs of Packaging, Ref. 89-030-2622, Maersk Medical A/S, Denmark.

(Continued)

*Primary Examiner* — Steven A. Reynolds
(74) *Attorney, Agent, or Firm* — Dickinson Wright PLLC

(57) ABSTRACT

A package for a multi-component medical device is disclosed. The package includes a bottom portion with cavities providing individual access to different components of the medical device, thereby enabling a user to remove components from the package in any order without disturbing the remaining component or components. The package also includes a barrier affixed to the bottom portion for sealing the package.

27 Claims, 25 Drawing Sheets

(56) References Cited

U.S. PATENT DOCUMENTS

| | | | |
|---|---|---|---|
| 4,501,363 A * | 2/1985 | Isbey, Jr. | 206/570 |
| D283,051 S * | 3/1986 | Fichera | D24/123 |
| 4,605,399 A | 8/1986 | Weston et al. | |
| 4,844,251 A * | 7/1989 | Gueret | 206/222 |
| 5,048,684 A | 9/1991 | Scott | |
| 5,318,543 A | 6/1994 | Ross et al. | |
| 5,350,059 A * | 9/1994 | Chester et al. | 206/63.5 |
| 5,379,895 A * | 1/1995 | Foslien | 206/363 |
| D355,600 S | 2/1995 | Ford | |
| 5,390,792 A * | 2/1995 | Van Ness et al. | 206/439 |
| 5,474,181 A | 12/1995 | Shillington et al. | |
| 5,485,917 A | 1/1996 | Early | |
| D371,071 S | 6/1996 | Ford | |
| 5,545,145 A | 8/1996 | Clinton et al. | |
| D373,527 S | 9/1996 | Phillips | |
| 5,582,599 A | 12/1996 | Daneshvar | |
| D380,272 S * | 6/1997 | Partika et al. | D24/229 |
| 5,779,053 A * | 7/1998 | Partika et al. | 206/570 |
| D396,632 S | 8/1998 | Lee | |
| 5,797,882 A | 8/1998 | Purdy et al. | |
| D405,688 S | 2/1999 | Lee et al. | |
| 5,868,245 A | 2/1999 | Alt | |
| 5,925,017 A | 7/1999 | Kriesel et al. | |
| 5,968,021 A | 10/1999 | Ejlersen | |
| D427,061 S | 6/2000 | Niksich | |
| 6,159,193 A | 12/2000 | Tuerk | |
| 6,293,925 B1 | 9/2001 | Safabash et al. | |
| D478,001 S | 11/2001 | Milan | |
| D471,641 S * | 3/2003 | McMichael et al. | D24/229 |
| D484,044 S | 12/2003 | Milan | |
| 6,830,562 B2 | 12/2004 | Mogensen et al. | |
| 6,921,383 B2 | 7/2005 | Vitello | |
| 7,100,771 B2 * | 9/2006 | Massengale | A61M 5/002 206/363 |
| 7,207,974 B2 | 4/2007 | Safabash et al. | |
| 7,401,703 B2 * | 7/2008 | McMichael | A61B 19/026 206/370 |
| D579,541 S | 10/2008 | Mogensen et al. | |
| 7,585,287 B2 | 9/2009 | Bresina et al. | |
| 7,621,395 B2 | 11/2009 | Mogensen et al. | |
| D606,856 S | 12/2009 | Ginsberg et al. | |
| 7,699,807 B2 | 4/2010 | Faust et al. | |
| 7,731,691 B2 | 6/2010 | Cote et al. | |
| D642,048 S * | 7/2011 | Ocampo et al. | D9/424 |
| 8,162,892 B2 | 4/2012 | Mogensen et al. | |
| 8,172,805 B2 | 5/2012 | Mogensen et al. | |
| 8,177,064 B2 * | 5/2012 | McCormick | A61B 50/33 206/370 |
| 8,231,602 B2 | 7/2012 | Anderson et al. | |
| D674,687 S | 1/2013 | Cote et al. | |
| 8,556,074 B2 * | 10/2013 | Turner | A61F 2/0095 206/339 |
| D692,749 S * | 11/2013 | Larson et al. | D9/424 |
| 8,746,452 B2 * | 6/2014 | Tomes et al. | 206/366 |
| 8,770,409 B2 * | 7/2014 | Cude | 206/557 |
| 2002/0185406 A1* | 12/2002 | Massengale | A61M 5/002 206/571 |
| 2003/0121810 A1* | 7/2003 | Roshdy | 206/363 |
| 2003/0121812 A1 | 7/2003 | Sprieck et al. | |
| 2003/0121821 A1* | 7/2003 | Roshdy | 206/570 |
| 2004/0004019 A1* | 1/2004 | Busch | A61B 17/3401 206/571 |
| 2004/0195145 A1 | 10/2004 | Roshdy | |
| 2005/0033430 A1* | 2/2005 | Powers | A61B 17/7059 623/17.11 |
| 2006/0058599 A1 | 3/2006 | Cummings et al. | |
| 2006/0282045 A1* | 12/2006 | Wilkinson | A61B 5/1405 604/198 |
| 2007/0185495 A1* | 8/2007 | Hess et al. | 606/93 |
| 2009/0218243 A1 | 9/2009 | Gyrn et al. | |
| 2010/0063457 A1 | 3/2010 | Crossman | |
| 2010/0179508 A1 | 7/2010 | Mogensen et al. | |
| 2010/0185178 A1 | 7/2010 | Sharp et al. | |
| 2010/0274200 A1 | 10/2010 | Nielsen | |
| 2011/0137257 A1 | 6/2011 | Gyrn et al. | |
| 2011/0226652 A1* | 9/2011 | Hickmott et al. | 206/438 |
| 2012/0022460 A1 | 1/2012 | Horvath et al. | |
| 2012/0029440 A1 | 2/2012 | Boyd et al. | |
| 2012/0080330 A1* | 4/2012 | Rush | B65D 1/24 206/305 |
| 2012/0150123 A1* | 6/2012 | Lawrence | A61M 5/158 604/180 |
| 2013/0066271 A1 | 3/2013 | West | |

FOREIGN PATENT DOCUMENTS

| | | |
|---|---|---|
| FR | 2775108 A1 | 8/1999 |
| GB | 2437923 | 11/2011 |
| JP | 3-240664 A | 10/1991 |
| JP | 05044111 | 5/1993 |
| JP | 09201369 | 8/1997 |
| JP | 2005506110 | 3/2005 |
| JP | 2008044644 | 2/2008 |
| JP | 2008538526 | 10/2008 |
| JP | 3155666 | 11/2009 |
| JP | 2012515613 | 7/2012 |
| WO | WO9109637 | 7/1991 |
| WO | WO9109639 | 7/1991 |
| WO | WO9742901 | 11/1997 |
| WO | WO9933504 | 7/1999 |
| WO | WO02083021 | 10/2002 |
| WO | WO2005046780 | 5/2005 |
| WO | WO2005046781 | 5/2005 |
| WO | WO2010090734 | 8/2010 |
| WO | WO2011146042 | 11/2011 |

OTHER PUBLICATIONS

Disetronic Ultraflex Subcutaneous Infusion Set, Photographs of Packaging, Ref. 1500133, Disetronic Medical Systems, Inc., St. Paul, MN.

Mio Infusion Set, Photographs of Packaging, Ref. MMT-923, Medtronic MiniMed, Northridge, CA.

Orbit 90 Infusion Set, Photographs of Packaging, Ref. P1861, ICU Medical, Inc., San Clemente, CA.

Orbit 90 Teflon Infusion Set Brochure, http://www.orbit90.ca/Teflon_2.jpg (last visited Feb. 27, 2013).

Sof-set Micro QR Infusion Set, Photographs of Packaging, Ref. MMT-320, MiniMed, Northridge, CA.

Spring Infusion Set, Spring Universal Infusion Set, YouTube Video, http://www.youtube.com/watch?feature=player_embedded&v=gWzGbeLDNsQ#t=20s (uploaded Oct. 26, 2011).

Spring Infusion Set, Unboxing the Spring Infusion Set, YouTube Video, http://www.youtube.com/watch?v=2zJcbHY3Y8I (uploaded Aug. 5, 2011).

Thinset Infusion Set, Photographs of Packaging, Applied Diabetes Research, Inc., Carrolton, TX.

\* cited by examiner

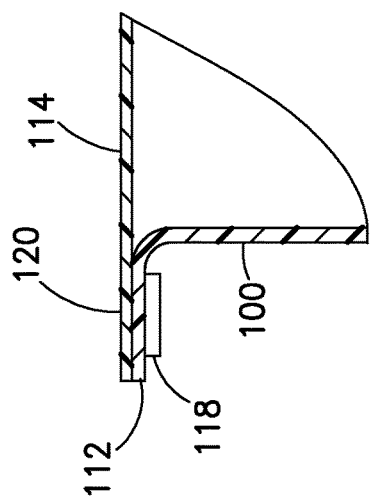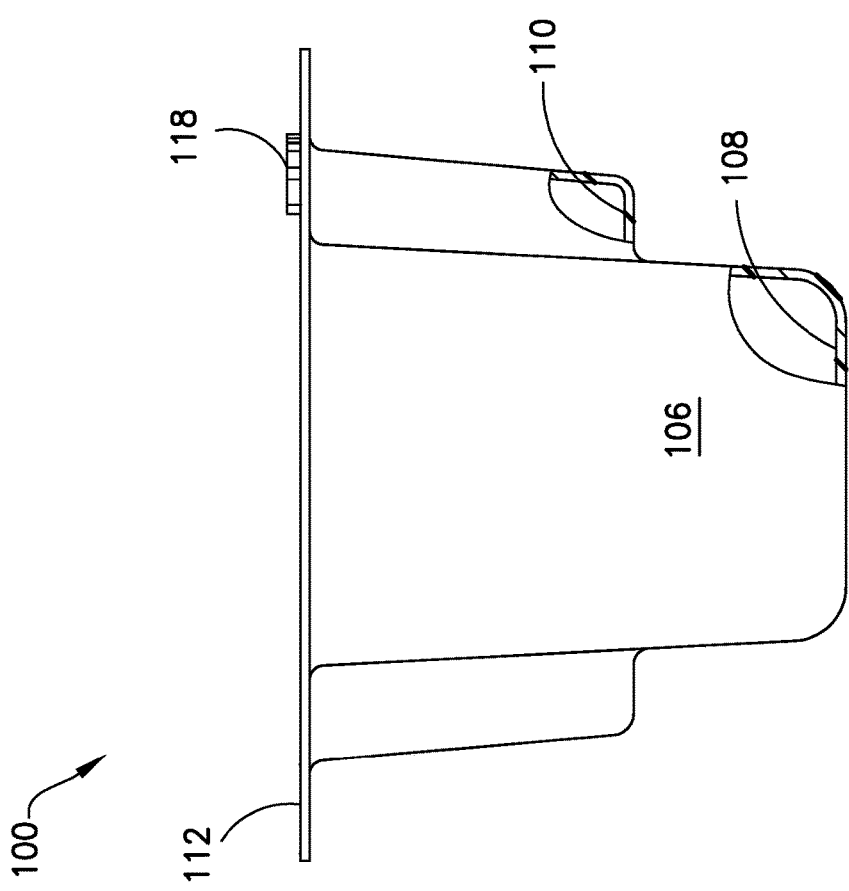

PACKAGE FOR MEDICAL PRODUCT

BACKGROUND OF THE INVENTION

1. Field of the Invention

The present invention relates to packaging, and more particularly, to a package for a medical product.

2. Description of the Related Art

Packaging for medical devices, particularly multi-component medical devices, such as insulin infusion devices, can include a breathable, sealable bag or pouch, or multiple packages for the complete set of components. Packaging can also include a base portion for housing the components along with a barrier that seals the housing portion. Although the process can be expensive, such housings are often injection molded to provide a desired shape for housing the components.

One problem with such bags or other packaging, however, is that the components are often placed together in a single compartment. Components can also shift location within the packaging during shipping. To access one of the components, the patient and/or other end user often must remove more than one, and sometimes all, of the components from the packaging. Additionally, the patient and/or other end user may be constrained to remove items in a particular order, even if that is not the order desired by the user. Although a user other than a patient (for example, a health care professional) can use a packaged medical product, for brevity the term "user" will be employed hereinafter to refer to a patient and/or other end user.

Moreover, with packages having removable sealing barriers, it is often difficult to open such packages, particularly if the user's dexterity is limited. Accordingly, to provide easy user access to a medical device, as well as protecting the device during shipping, improvements in the packaging of medical products is needed.

SUMMARY OF EMBODIMENTS OF THE INVENTION

Accordingly, it is an aspect of the present invention to provide improved packaging for medical products.

The foregoing and/or other aspects of the present invention are achieved by providing a package for a multi-component medical device, including a bottom portion with cavities providing individual access to different components of the medical device, thereby enabling a user to remove components from the package in any order without disturbing the remaining component or components. The package also includes a barrier affixed to the bottom portion for sealing the package.

The foregoing and/or other aspects of the present invention are also achieved by providing a method of packaging a multi-component medical device. The method includes forming a bottom portion with cavities that provide individual access to different components of the medical device, thereby enabling a user to remove components from the package in any order without disturbing the remaining component or components. The method also includes affixing a barrier to a rim of the bottom portion to seal the package.

The foregoing and/or other aspects of the present invention are also achieved by providing a package for a medical device. The package includes a bottom portion that includes at least one cavity for housing the medical device, and a flange providing a sealing surface. The package also includes a barrier affixed to the flange for sealing the package. The flange includes an informational marking that is raised relative to the remainder of the flange to provide a lifting tab of the barrier when the barrier is affixed to the flange of the bottom portion.

The foregoing and/or other aspects of the present invention are also achieved by providing a package for a multi-component medical device. The package includes a bottom portion having at least one cavity for housing the medical device, a platform insertable into the cavity, for raising at least one of the components of the medical device above a floor of the cavity, and a barrier affixed to the bottom portion for sealing the package.

The foregoing and/or other aspects of the present invention are also achieved by providing a package for a medical device. The package includes a bottom portion that includes at least one cavity for housing the medical device, and a flange providing a sealing surface. The package also includes a barrier affixed to the flange for sealing the package. The flange includes an informational marking that is recessed relative to the flange to provide a lifting tab for the barrier when the barrier is affixed to the flange of the bottom portion.

The foregoing and/or other aspects of the present invention are also achieved by providing a package for a medical device. The package includes a bottom portion that includes at least one cavity for housing the medical device, and a flange providing a sealing surface. The package also includes a barrier affixed to the flange for sealing the package. The flange includes a recessed portion to provide a lifting tab for the barrier when the barrier is affixed to the flange of the bottom portion, and the recessed portion includes a marking that is recessed from the recessed portion.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which:

FIG. 2 is a front view of the bottom portion of FIG. 1;

FIG. 5B is a partial side view of a package including an alternative embodiment of a bottom portion in accordance with an embodiment of the present invention;

DETAILED DESCRIPTION OF EMBODIMENTS OF THE PRESENT INVENTION

Figure 1:
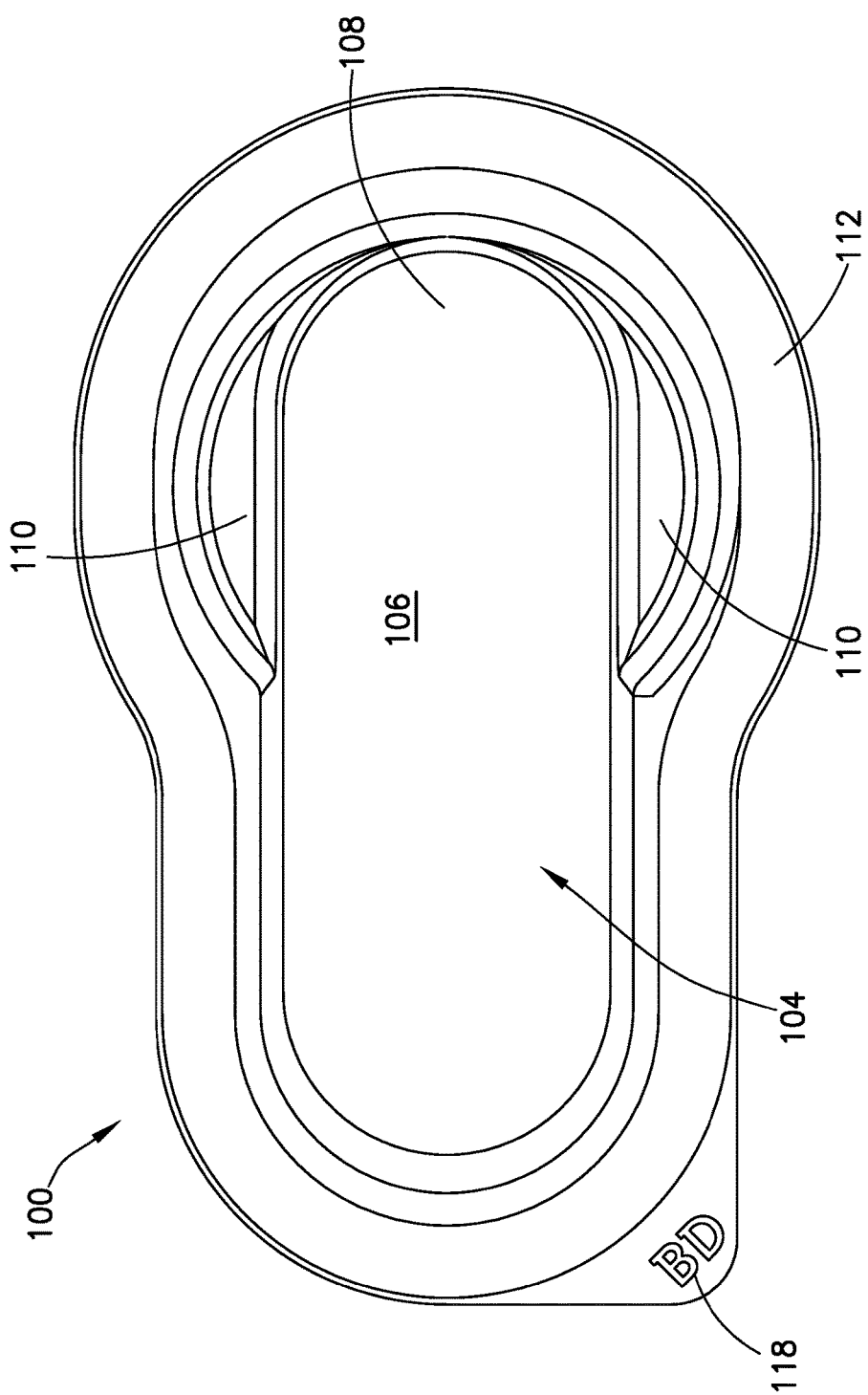
FIG. 1 is a top view of a bottom portion of a package in accordance with an embodiment of the present invention.

Reference will now be made in detail to embodiments of the present invention, which are illustrated in the accompanying drawings, wherein like reference numerals refer to like elements throughout. The embodiments described herein exemplify, but do not limit, the present invention by referring to the drawings. As will be understood by one skilled in the art, terms such as up, down, bottom, top, above, and below are relative, and are employed to aid illustration, but are not limiting.

Figure 3:
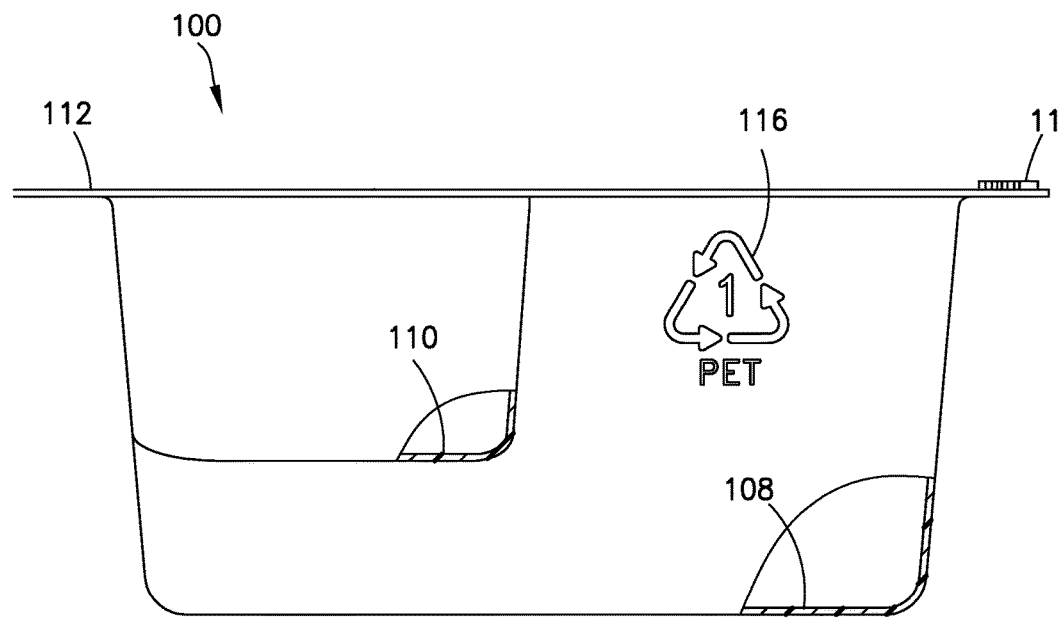
FIG. 3 is a left side view of the bottom portion of FIG. 1.
Figure 4:
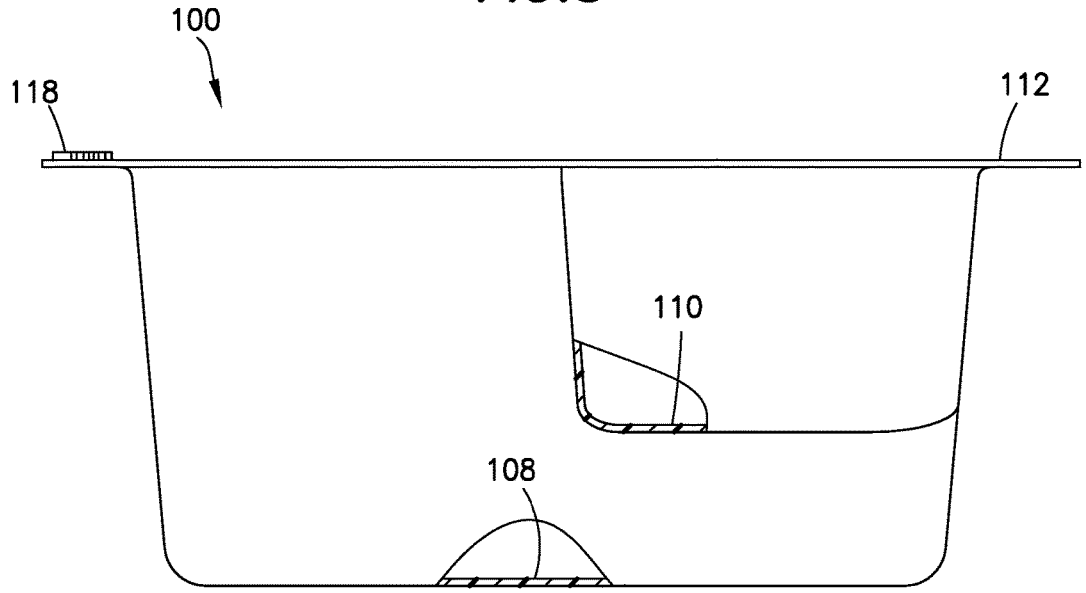
FIG. 4 is a right side view of the bottom portion of FIG. 1.

FIG. 1 is a top view of a bottom portion 100 of a package 102 in accordance with an embodiment of the present invention. FIG. 2 is a front view of the bottom portion 100, and FIGS. 3 and 4 are respective left and right views of the bottom portion 100. The bottom portion 100 is transparent and includes a cavity 104 for holding or housing a medical product, for example, a multi-component medical device. As subsequently described in greater detail, the cavity 104 includes a main portion 106 with a floor 108, and a platform or shelf 110 that is raised above the floor 108.

Figure 5A:
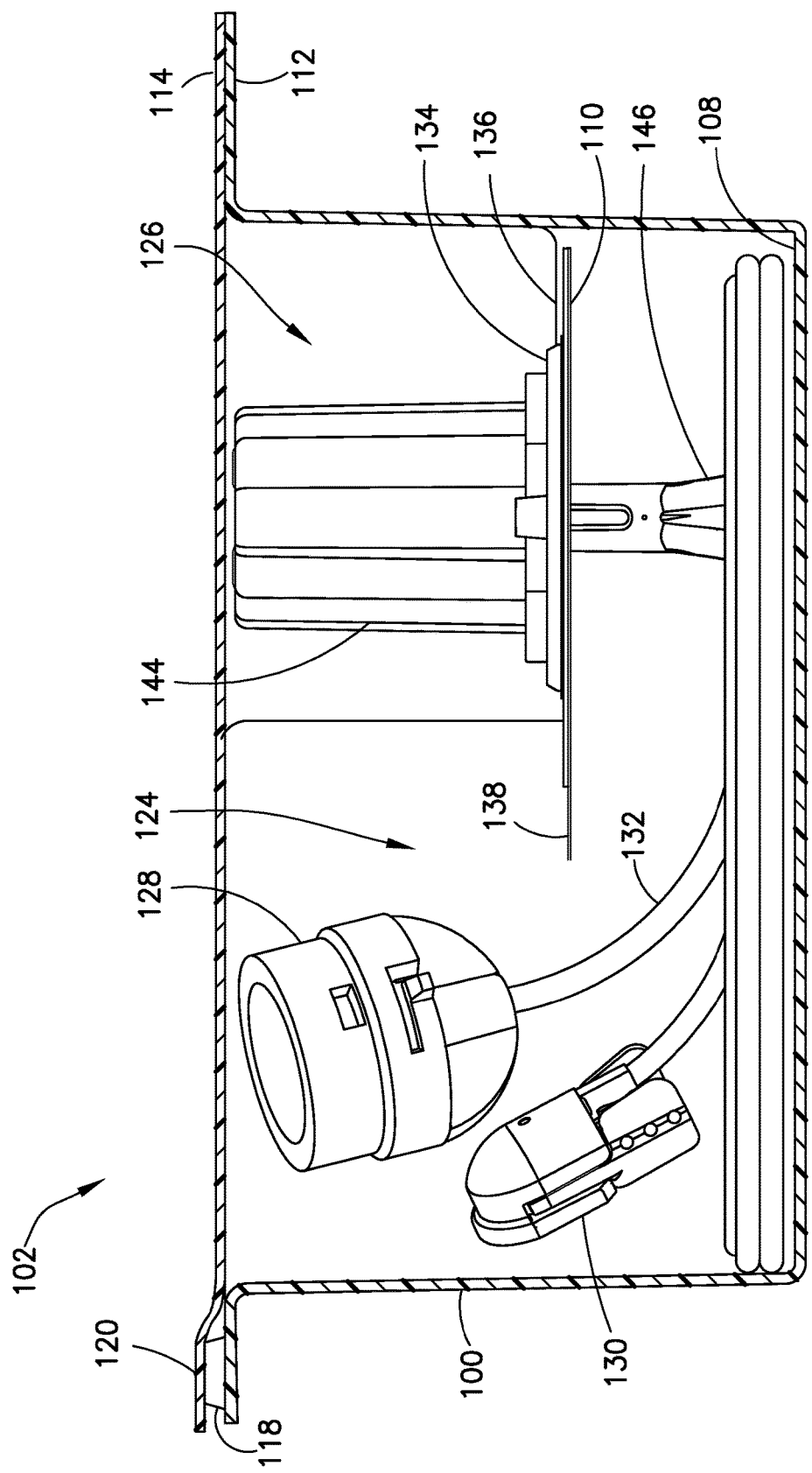
FIG. 5A is a side view of a package including the bottom portion of FIG. 1 with a medical device disposed therein in accordance with an embodiment of the present invention.

The bottom portion 100 also includes a flange 112 that provides a sealing surface for a barrier 114 (see, for example, FIG. 5A). The barrier 114 is preferably gas-permeable, so that subsequent to sealing, the contents of the package 102 can be sterilized with gas. For example, the barrier 114 can be Tyvek® material. Preferably, however, the barrier 114 is paper coated with an adhesive polymer on one side for securing the barrier 114 to the bottom portion 100. A heat press can be used to secure the barrier 114 to the bottom portion 114. One skilled in the art will appreciate that other methods of securing the barrier 114 to the flange 112 can be implemented without departing from the scope of the present invention. As an alternative to gas sterilization, the package 102 and its contents can be irradiated.

Preferably, the bottom portion 100 is theremoformed using transparent polyethylene terephthalate (PET) film. More preferably, the PET is an amorphous PET (APET). Most preferably, the bottom portion is made of Pentamed® TerraPET® film, which is available from Klöckner Pentaplast. TerraPET® film is a sterilizable rigid APET film that is made with up to 30% renewable resource content. More specifically, TerraPET® film is made from two raw materials, one of which is derived from ethanol rather than petroleum. Heretofore, TerraPET® has not been used in medical device packaging on the market.

One advantage of using PET is to allow the embossing of informational markings, symbols, or characters during the thermoforming process. For example, as shown in FIG. 3, a recycling indicator 116 can be formed in a side wall of the bottom portion 102. In addition, one or more alphanumeric characters or logos 118 can be formed, for example, by embossing, in the flange 112. Such informational markings 118 can serve several purposes. A character or logo 118 can illustrate a trademark or advertising, for example, to represent the source of the product housed in the bottom portion 102. Alternatively, the informational marking 118 can provide instructions, such as a direction for removing the barrier 114.

As another example, according to an embodiment best shown in FIG. 5A, the informational marking 118 can be raised relative to the flange 112 to provide a location of a lifting tab 120 of the barrier 114 when the barrier 114 is connected to the bottom portion 100. Preferably, adhesive is not applied to the raised informational marking 118 when the barrier 114 is secured to the bottom portion 100, thereby providing the lifting tab 120. Even if adhesive is applied to the informational marking 118, however, because the informational marking 118 is raised relative to the flange 112, this provides an area (surrounding the informational marking 118) in which the barrier is not secured to the flange 112. Thus, the user is more easily able to lift the lifting tab 120.

As an alternative, however, the informational marking 118 can also be recessed relative to the flange 112, as shown in FIG. 5B. As noted previously, it is preferable that the barrier 114 is paper with an adhesive polymer on one side thereof. More preferably, the adhesive polymer is a heat-activated adhesive polymer, so that the barrier 114 can be secured to the bottom portion 100, for example, on the flange 112, using a heat press. Having the informational marking 118 recessed below the flange 112 allows the heat press to have a flat surface. Preferably, however, the informational marking 118 still provides a lifting tab 120 for the barrier; the adhesive does not adhere to the informational marking 118 because it is recessed.

Referring back to FIG. 5A, the package 102, which includes the bottom portion 100 and the barrier 114, can house a multi-component medical device 122, such as an infusion set 122. The device 122 includes a line set or tubing set 124 and an insertion set or introducer assembly 126. The line set 124 includes a pump connector 128 for connecting to a pump, a fluid connector for connecting to a base, and tubing 132 connecting the pump connector 128 to the fluid connector 130.

The insertion set includes a base 134 with an adhesive pad 136 secured to its distal side for securing the device 122 to a patient's skin. The adhesive pad 136 has a removable liner 138 to protect the patient-side adhesive. An insertable cannula 140 (see, for example, FIG. 11) depends from the distal side of the base 134. According to one embodiment, the cannula 140 is a flexible cannula and the device 122 includes an introducer needle 142 (see, for example, FIG. 11) with a user interface or handle 144 for removing the introducer needle 142 from the base 134. One skilled in the art will appreciate, however, that other types of cannulas, such as rigid steel needles that do not require a separate introducer, can be used without departing from the scope of the present invention.

The medical device 122 also includes a removable needle guard 146 to protect the cannula and the introducer needle prior to use, and to shield the introducer needle subsequent to removal of the introducer needle from the base 134. The length of the cannula 140 can vary depending on desired insertion depth and desired depth for delivery of a medicament. For example, the cannula 140 can be 6 mm or 9 mm. The length of the needle guard 146 can vary accordingly. The device 122 can also include a sterile cover 148 (see, for example, FIG. 16) for covering a port of the base when the fluid connector 130 is not connected to the port, for example, when bathing or swimming.

The cavity 104 of the bottom portion 100 provides a space to house the line set 124, with the tubing 132 resting on the floor 108, and the platform 110 houses the insertion set 126, providing clearance for the needle guard 146 below the level of the platform 110.

Figure 6:
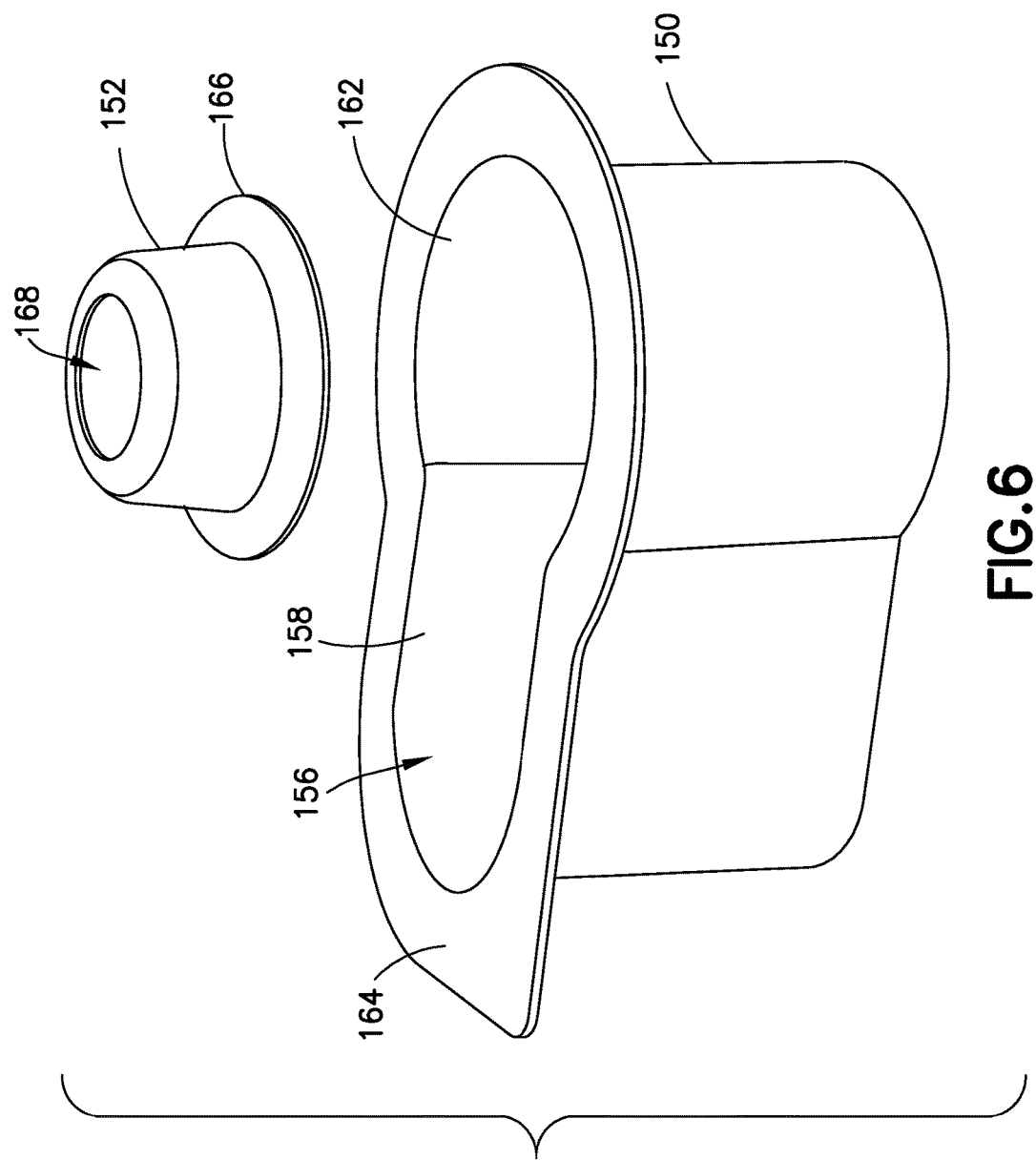
FIG. 6 is an exploded perspective view of a bottom portion and a platform of a package in accordance with another embodiment of the present invention.
Figure 7:
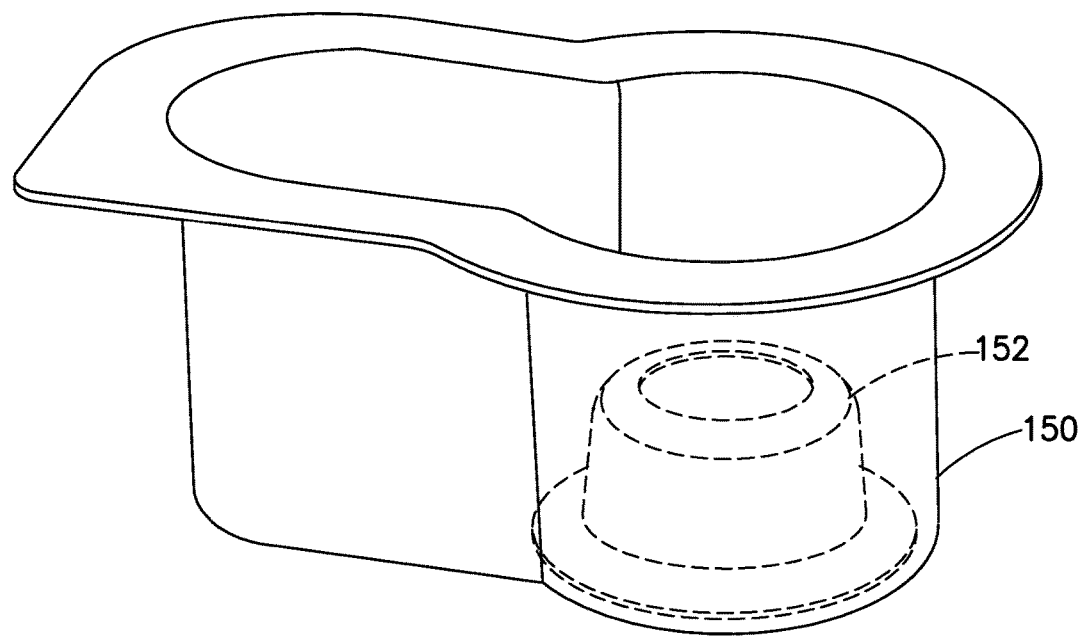
FIG. 7 is a perspective view of the elements of FIG. 6 in an assembled state.
Figure 8:
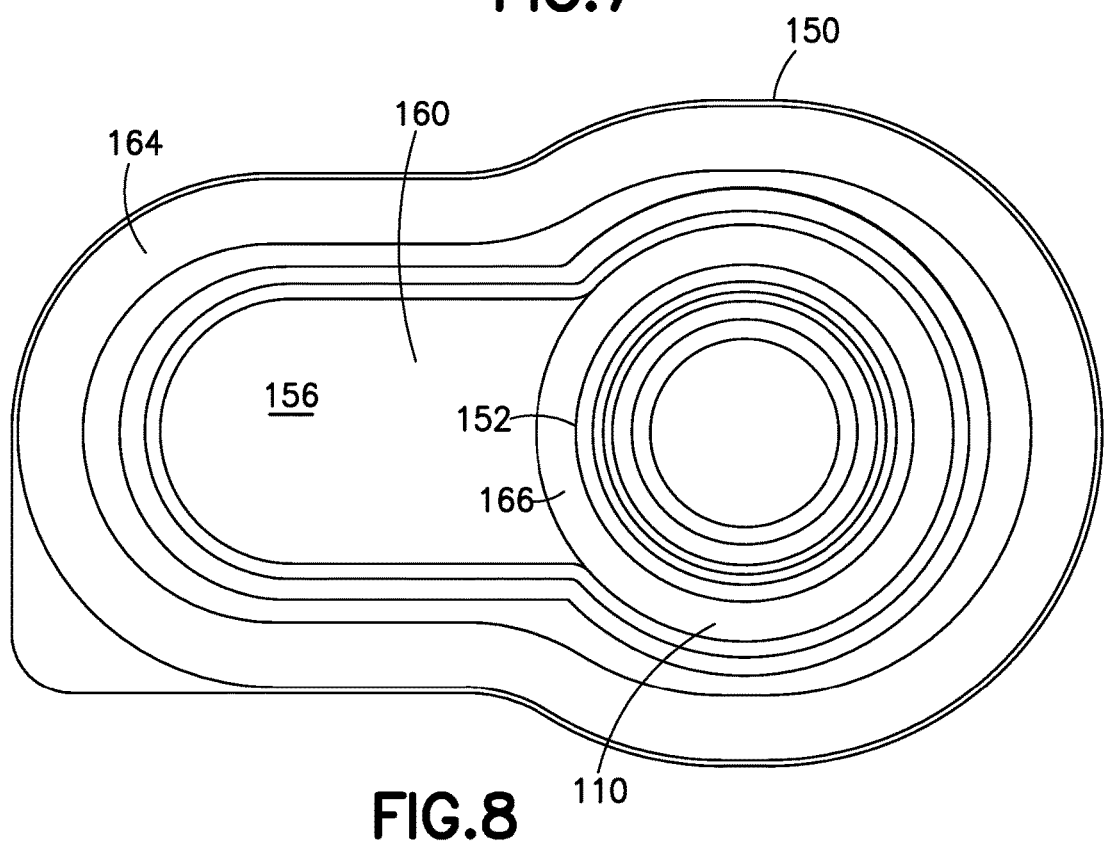
FIG. 8 is a top view of the assembled elements of FIG. 6.
Figure 9:
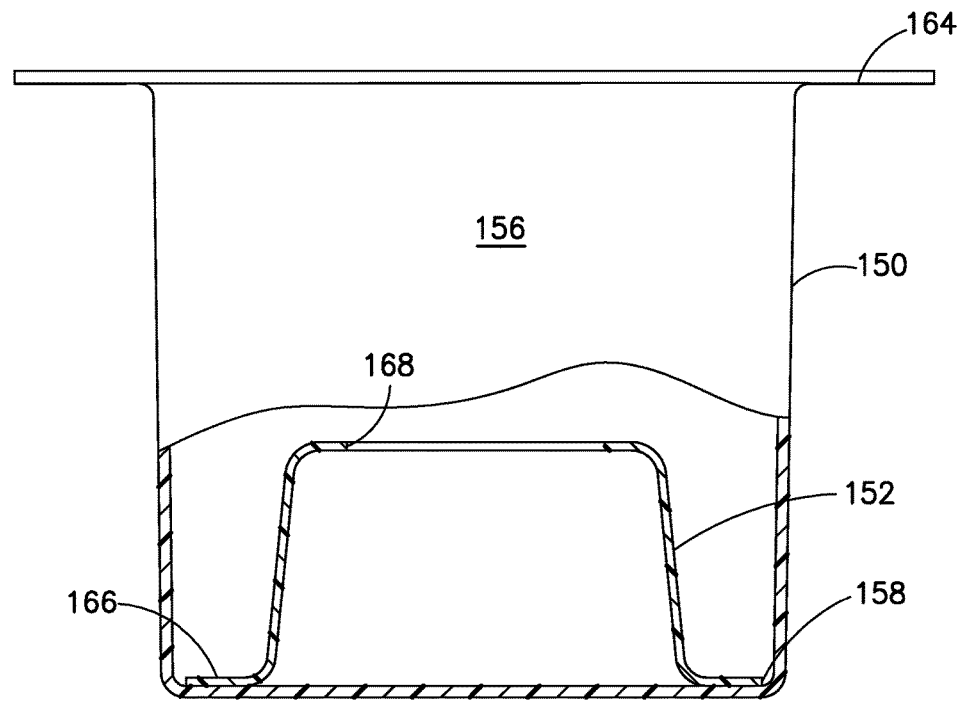
FIG. 9 is a rear view of the assembled elements of FIG. 6.
Figure 10:
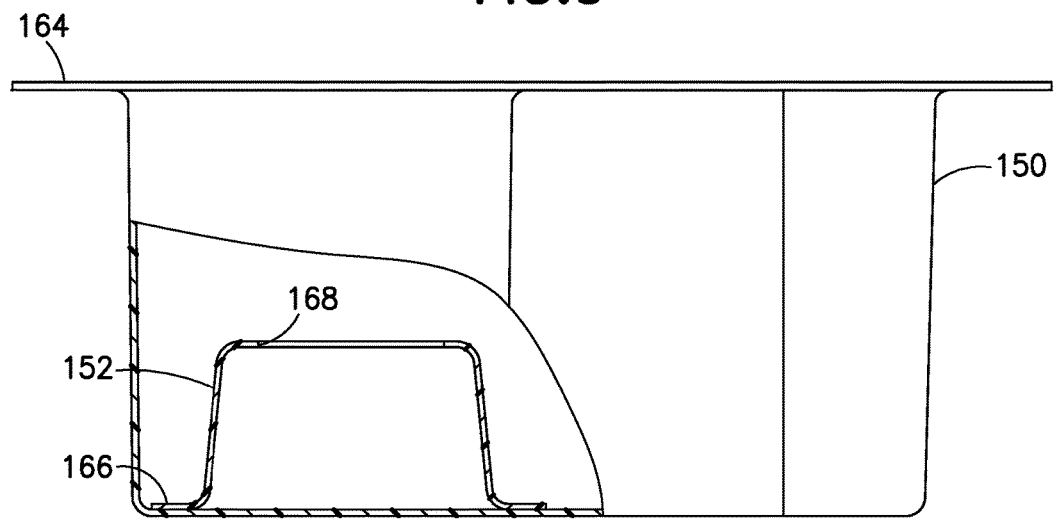
FIG. 10 is a right side view of the assembled elements of FIG. 6.

FIG. 6 is an exploded perspective view of a bottom portion 150 and a platform 152 of a package 154 in accordance with another embodiment of the present invention, and FIG. 7 is a perspective view of the bottom portion 150 and the platform 152 in an assembled state. FIGS. 8-10 are respective top, rear, and right side views of the assembled bottom portion 150 and platform 152.

Like the previously-described bottom portion 100, the bottom portion 150 is transparent and includes a cavity 156 for holding or housing a medical product, for example, a multi-component medical device. The cavity 156 includes a main portion 158 with a floor 160 and a platform portion 162 for receiving the platform 152, which is also preferably transparent. The bottom portion also includes a flange 164 for receiving the barrier 114.

The platform 152 has a platform flange 166. According to one embodiment, the platform 152 has an opening 168 on the top thereof and is hollow. Preferably, the bottom of the platform is also open. The platform portion 162 of the platform portion 162 has a shape that corresponds to the platform flange 166, and thus, once the platform 152 is inserted into the platform portion 162, the platform portion retains the platform flange 166 and substantially prevents lateral movement of the platform 152 relative to the bottom portion 150. The corresponding shapes can be multifaceted, for example, triangular, rectangular, or the like, or the corresponding shapes can be rounded, for example, elliptical, ovoid, circular, conical, or, as shown in FIGS. 6-12, frusto-conical.

According to one embodiment, the platform portion 162 of the bottom portion 150 also has a retaining rim disposed near the floor 160 to vertically retain the platform flange 166. As the platform 152 is inserted into the platform portion and the platform flange 166 engages the retaining rim, at least one of the flange 166 and the rim deforms or deflects to permit relative displacement. According to one embodiment, the retaining rim and the platform flange 166 provide a snap-fit engagement to retain the platform 152 in the bottom portion subsequent to its installation therein. According to one embodiment, the retaining rim is discontinuous, thereby providing a plurality of retaining rims arrayed around the perimeter (for example, the circumference) of the platform portion 162. According to one embodiment, however, there is no retaining rim, and although the platform portion 162 prevents lateral movement of the platform 152 relative to the bottom portion 150, the platform 152 is not prevented from displacing vertically.

Figure 11:
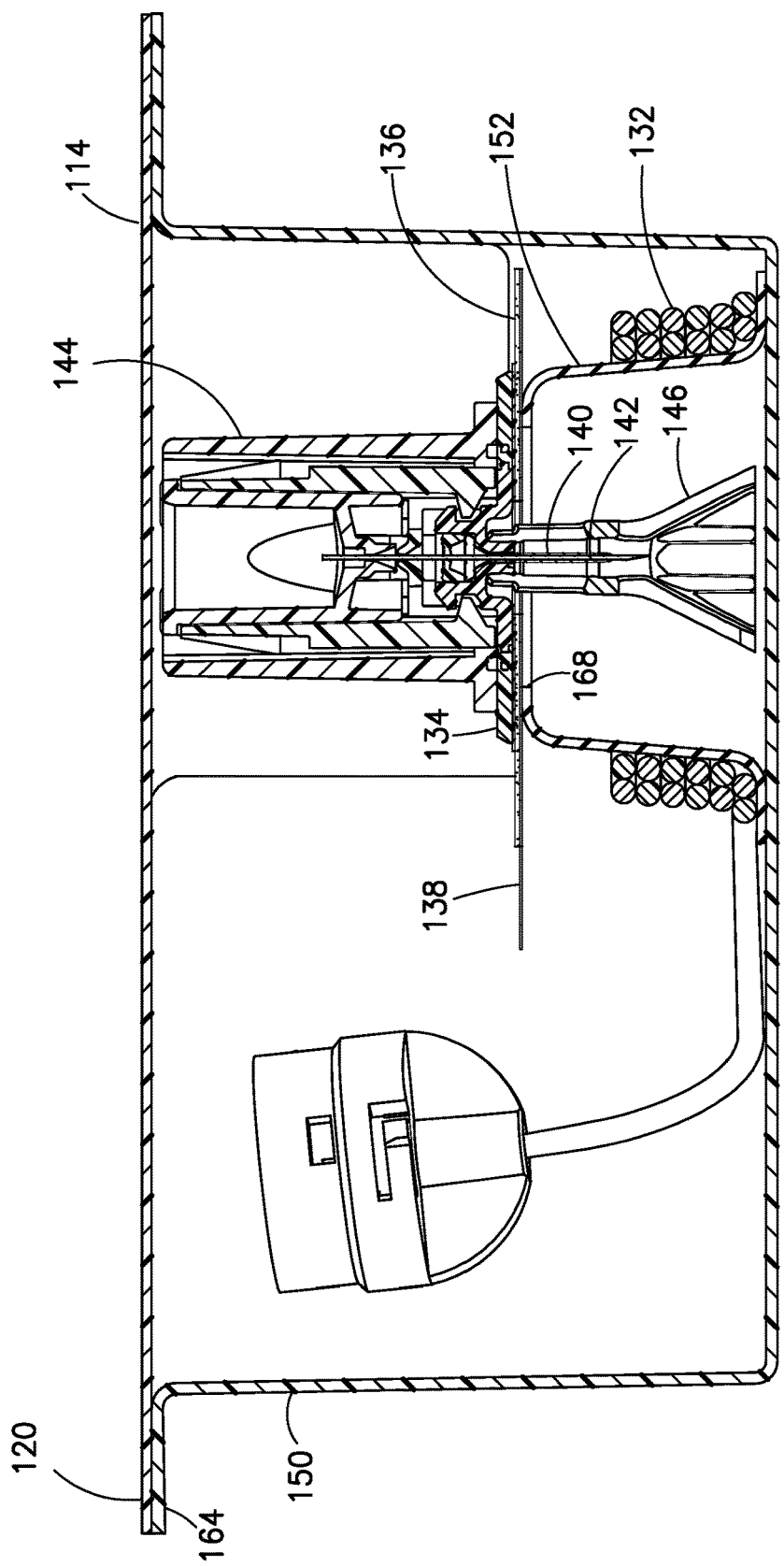
FIG. 11 is a cross-sectional view of a package including the assembled elements of FIG. 6 with a medical device disposed therein in accordance with an embodiment of the present invention.
Figure 12:
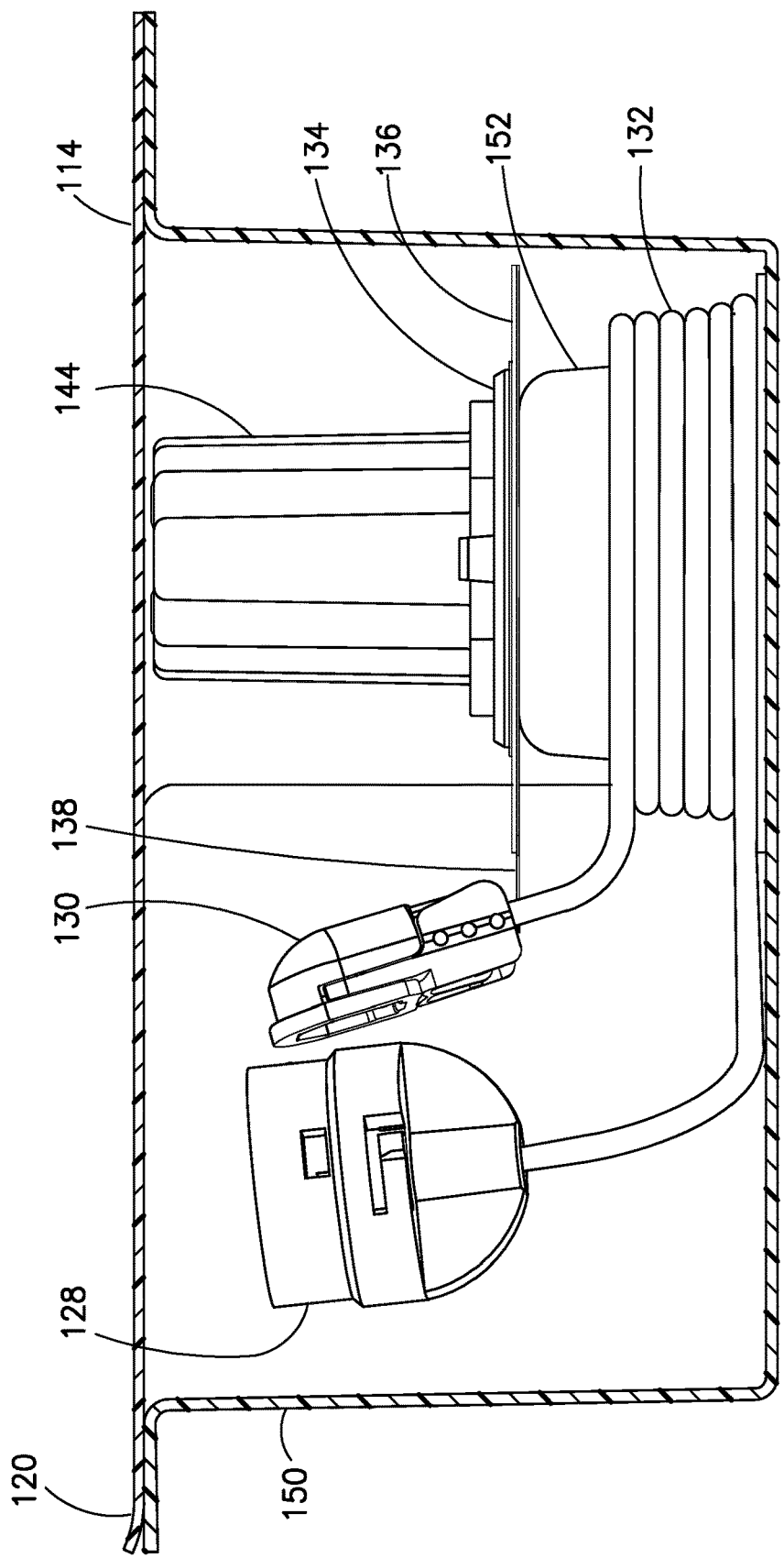
FIG. 12 is a side view of the package and medical device of FIG. 11.

As best shown in FIGS. 11 and 12, which illustrate the barrier 114 connected with the bottom portion 150, when housing the infusion set 122, the tubing 132 coils around the platform 152, and the insertion set 126 rests on top of the platform 152, with the needle guard 146 extending through the opening 168 in the top of the platform 152.

Figure 13:
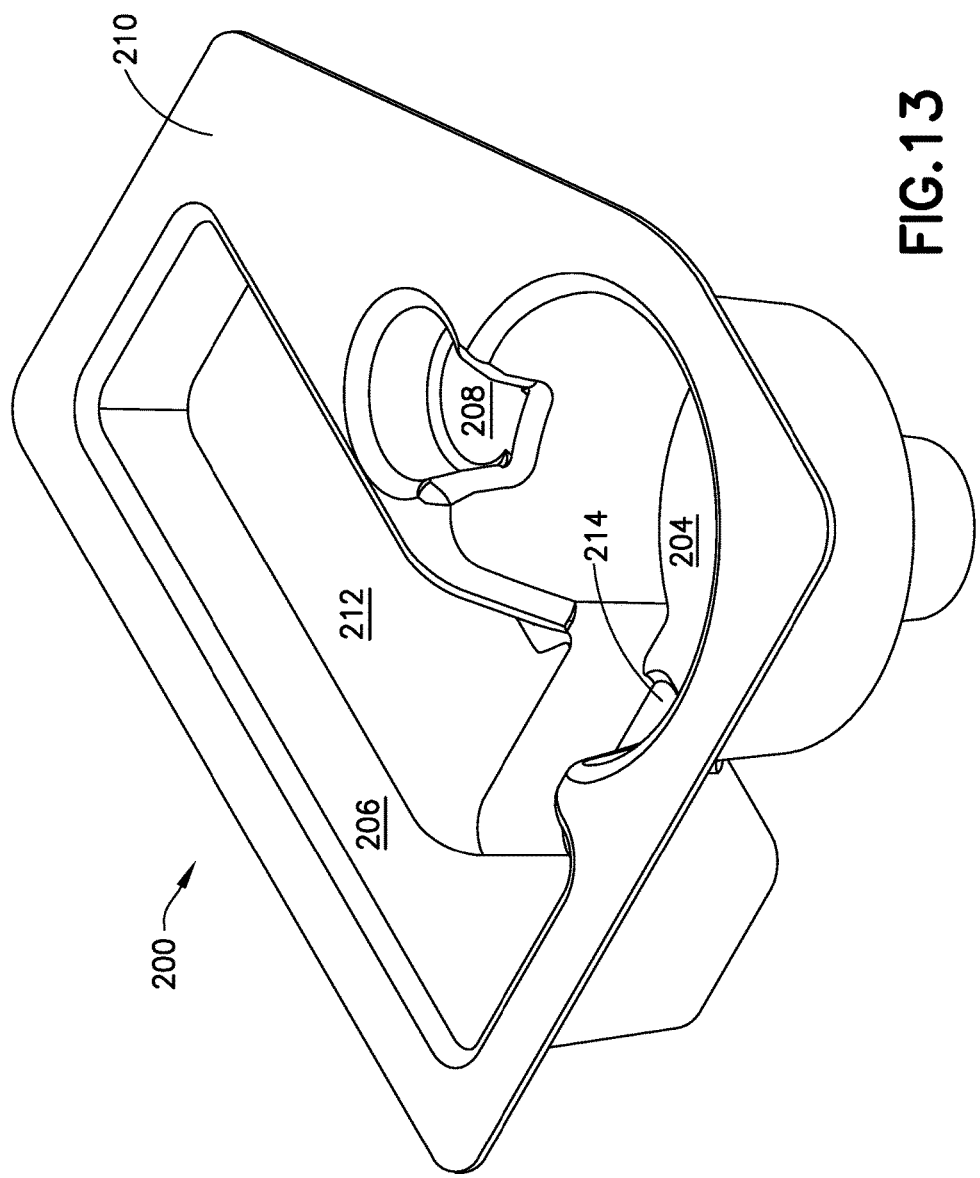
FIG. 13 is a perspective view of a bottom portion of a package in accordance with another embodiment of the present invention.
Figure 14:
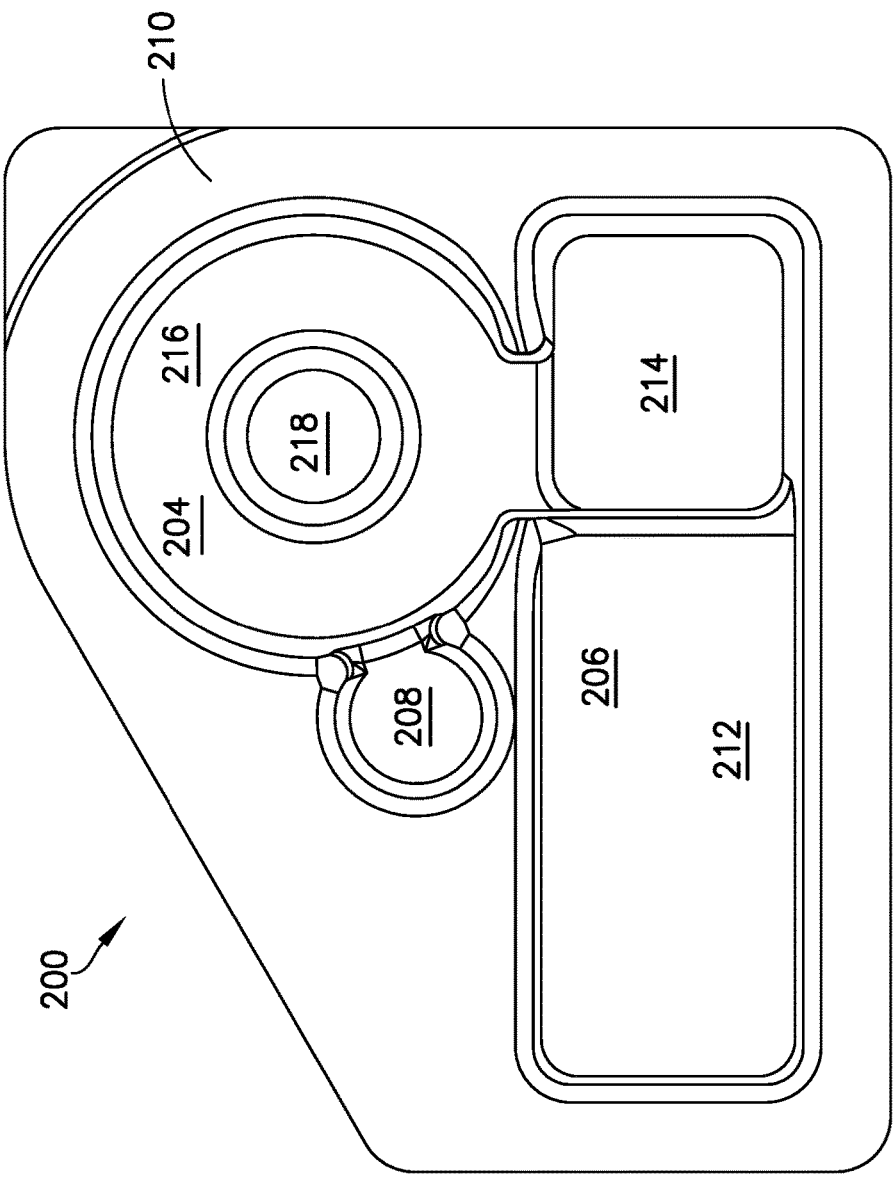
FIG. 14 is a top view of the bottom portion of FIG. 13.
Figure 15:
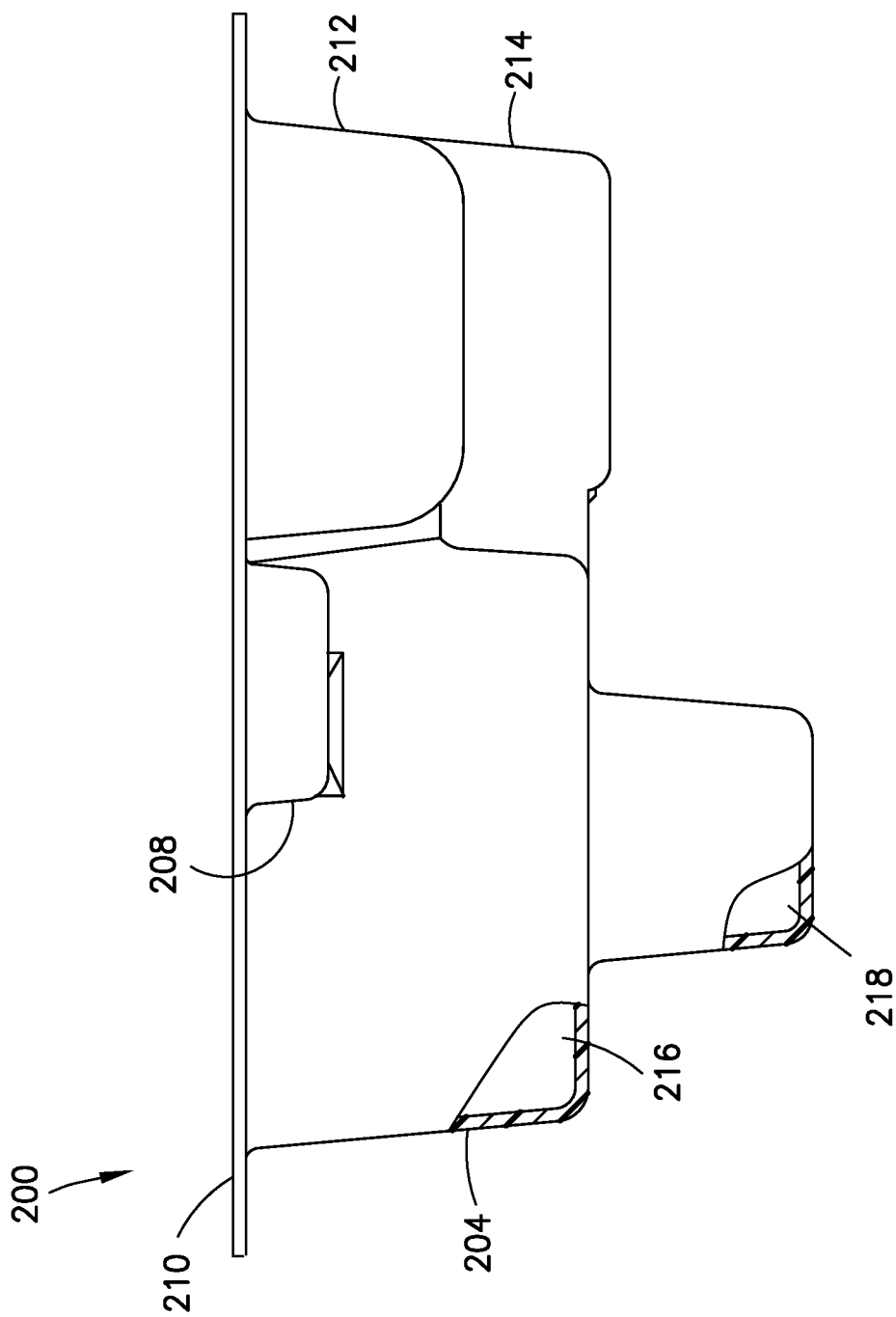
FIG. 15 is a right side view of the bottom portion of FIG. 13.
Figure 16:
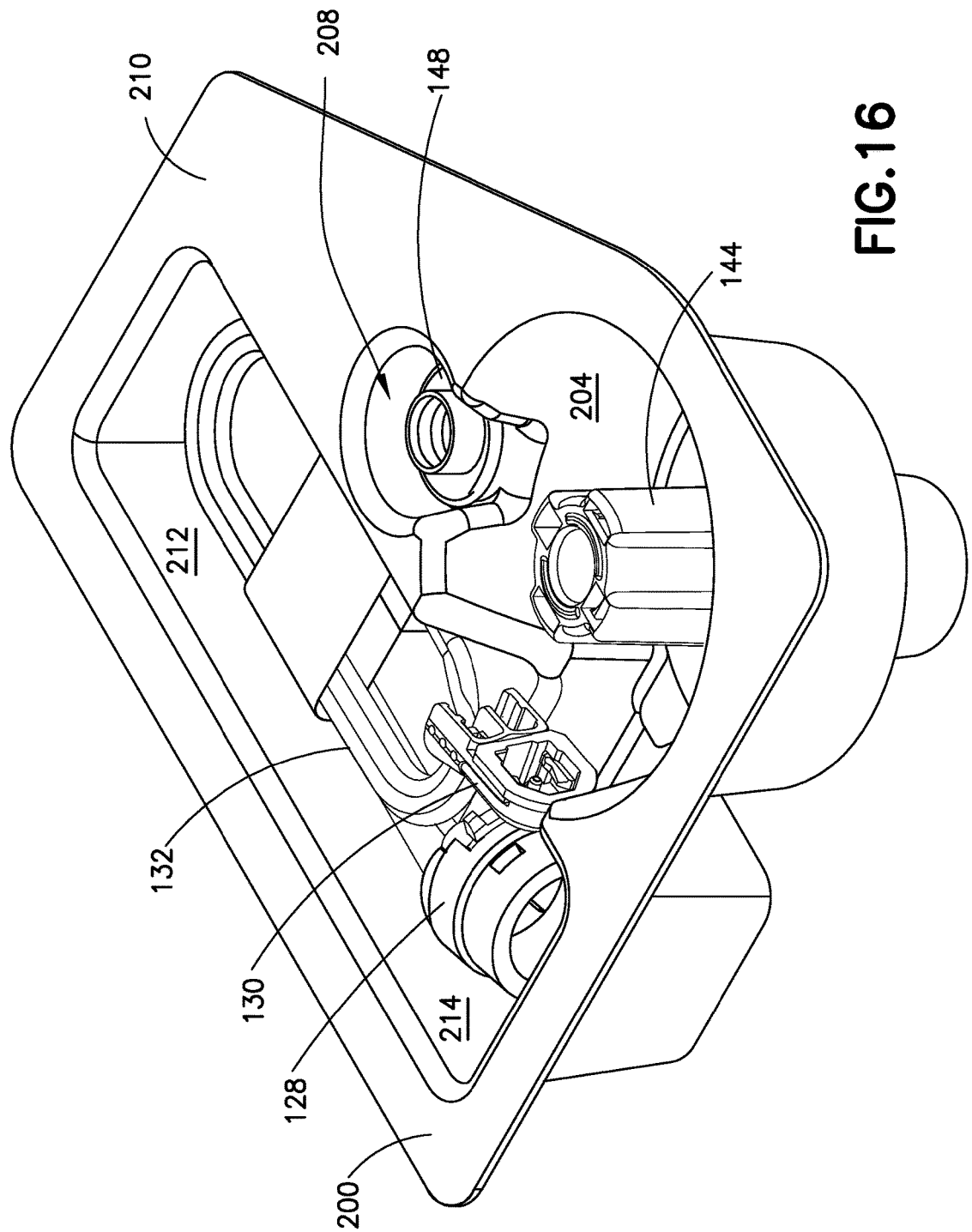
FIG. 16 is a perspective view of the bottom portion of FIG. 13 with a medical device disposed therein in accordance with an embodiment of the present invention.
Figure 17:
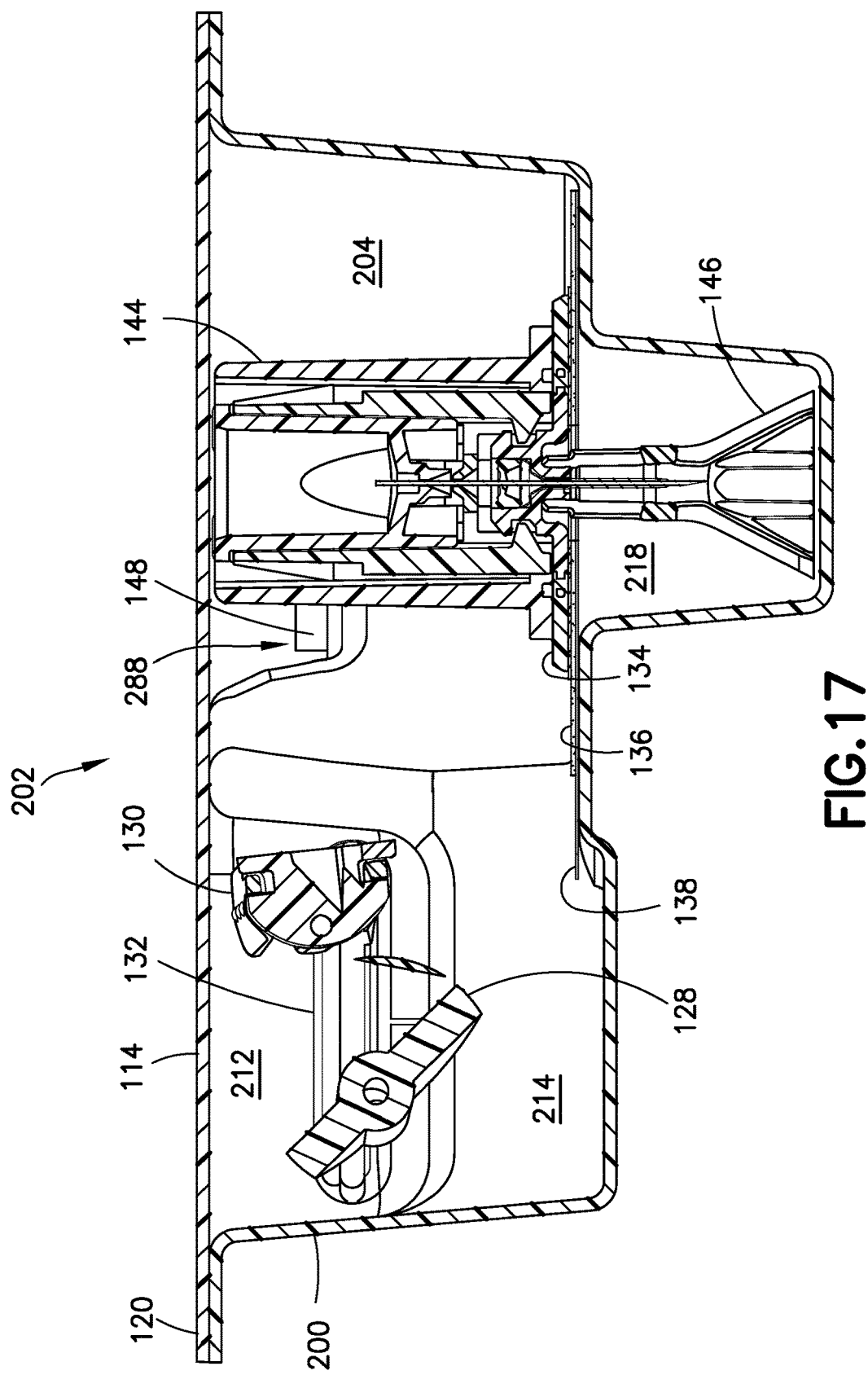
FIG. 17 is a cross-sectional view of a package including the bottom portion of FIG. 13 with a medical device disposed therein in accordance with an embodiment of the present invention.

FIG. 13 is a perspective view of a bottom portion 200 of a package 202 in accordance with another embodiment of the present invention. FIGS. 14 and 15 are respective top and right side views of the bottom portion 200. FIG. 16 is a perspective view of the bottom portion with the medical device 122 disposed therein, and FIG. 17 is a cross-sectional view of the package 202 (including the bottom portion 200 and the barrier 114) with the medical device 122 disposed therein.

The bottom portion 200 is transparent and has a plurality of cavities that are organized into regions for each component of the multi-component medical device 122. In other words, the bottom portion 200 includes a designated region for each component. This arrangement provides individual access to different components of the medical device 122, thereby enabling the user to remove components from the package 202 in any order without disturbing the remaining component(s).

For example, the bottom portion 200 includes a region 204 for the insertion set or introducer assembly 126, a region 206 for the line set or infusion tubing set 124, and a region 208 for the sterile cover 148. Each of these regions 204, 206, and 208 are recessed from an upper surface 210 of the bottom portion 200. In this embodiment, the upper surface 210 is a flange 210.

Preferably, the infusion tubing set region 206 includes a first or tubing region 212 designated to house the tubing 132, and a second or connector region 214 designated to house the pump connector 128 and the fluid connector 130. As shown most clearly in FIG. 15, the connector region 214 is recessed further from the flange 210 than the tubing region 212.

In addition, the introducer assembly region 204 preferably includes a pair of substantially concentric recesses: a handle recess 216 with a bottom forming a platform for receiving the adhesive liner 138, and a guard recess 218 for receiving the needle guard 146. The majority of the handle recess 216 is enclosed, thereby preventing lateral movement of the introducer assembly of insertion set 126 when it is disposed within the introducer assembly region 204. As best shown in FIG. 15, the guard recess 218 is recessed farther from the flange 210 than the handle recess 216.

As shown in FIGS. 13-17, the introducer assembly region 204 is contiguous with both the sterile cap region 208 and the connector region 214, which is a part of the tubing set region 206. In this embodiment, however, the sterile cap region 210 is not contiguous with the connector region 214 or the tubing region 212. This arrangement allows the user to remove components from the package 202 in any order without disturbing the remaining component(s). One skilled in the art will appreciate that the contiguity and recess depth of the various regions can be altered without departing from the scope of the present invention.

Figure 18:
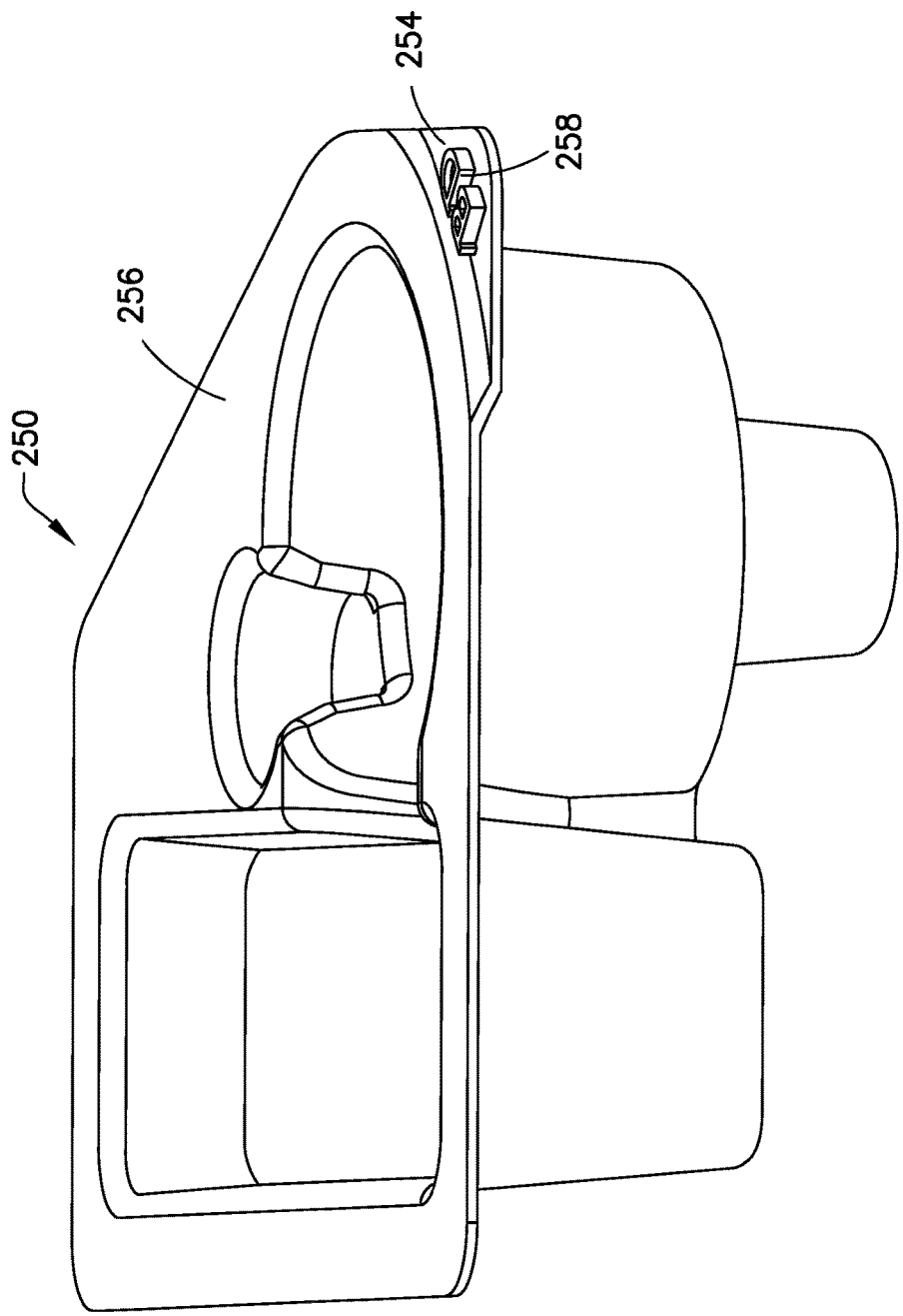
FIG. 18 is a perspective view of a bottom portion of a package in accordance with another embodiment of the present invention.
Figure 19:
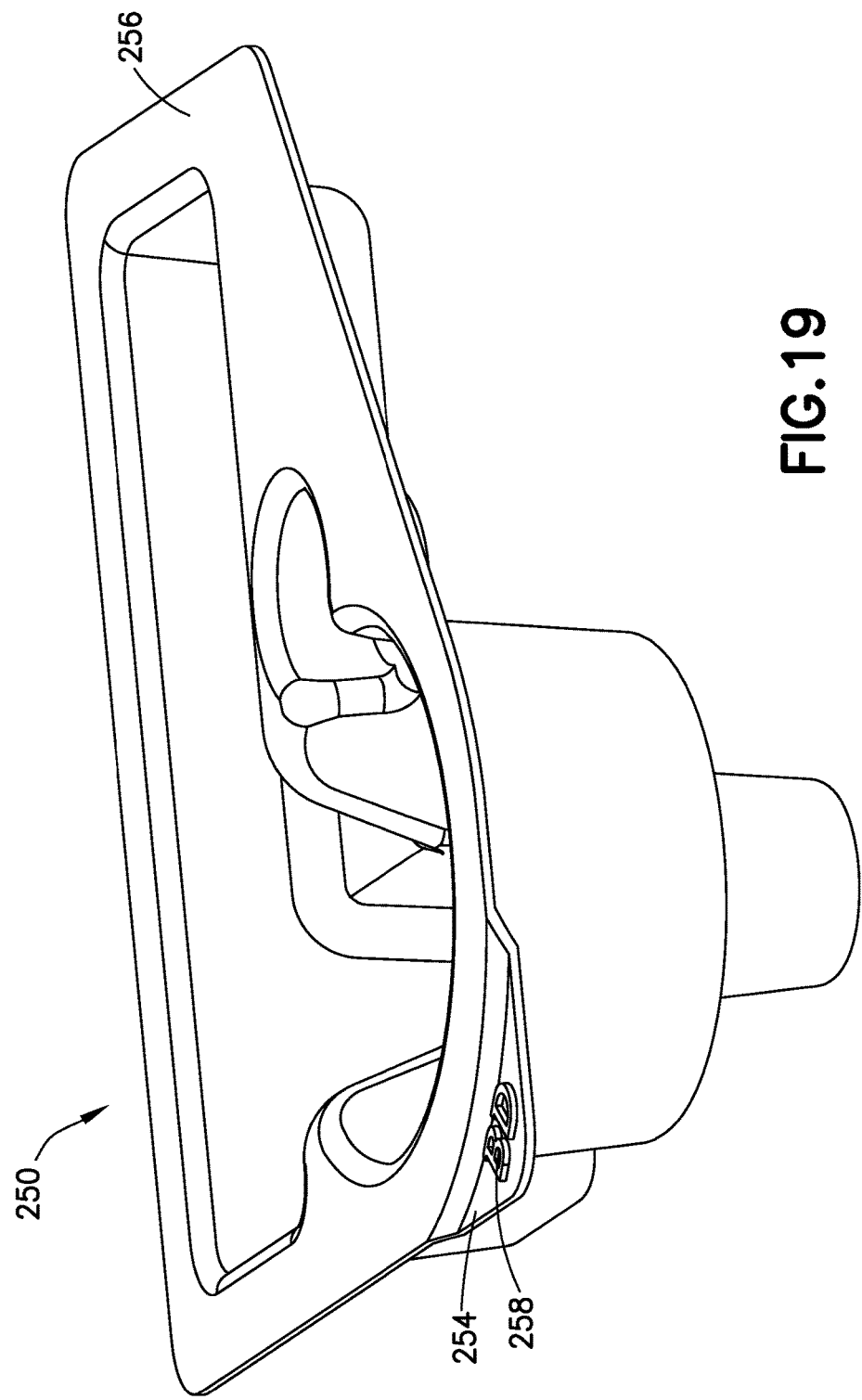
FIG. 19 is another perspective view of the bottom portion of FIG. 18.

FIGS. 18 and 19 are perspective views of a bottom portion 250 of a package 252 in accordance with another embodiment of the present invention. The bottom portion 250 is transparent and is substantially similar to the bottom portion 200, except that a portion 254 of the flange 256 is recessed below the flange 256. This recessed portion 254 provides a location for the lifting tab 120 of the barrier 114. In other words, the barrier 114 is preferably not adhered to the recessed portion 254. Put another way, the flange 256 provides a surface for adhering the barrier 114, thereby sealing the contents of the package 252. But because the portion 254 is recessed, when the preferably flat heat press activates the adhesive of the barrier 114 and seals the barrier 114 onto the flange 256, the barrier is preferably not pressed against the recessed portion 254. Thus, the portion of the barrier 114 above the recessed portion 254 becomes the lifting tab 120.

Figure 20:
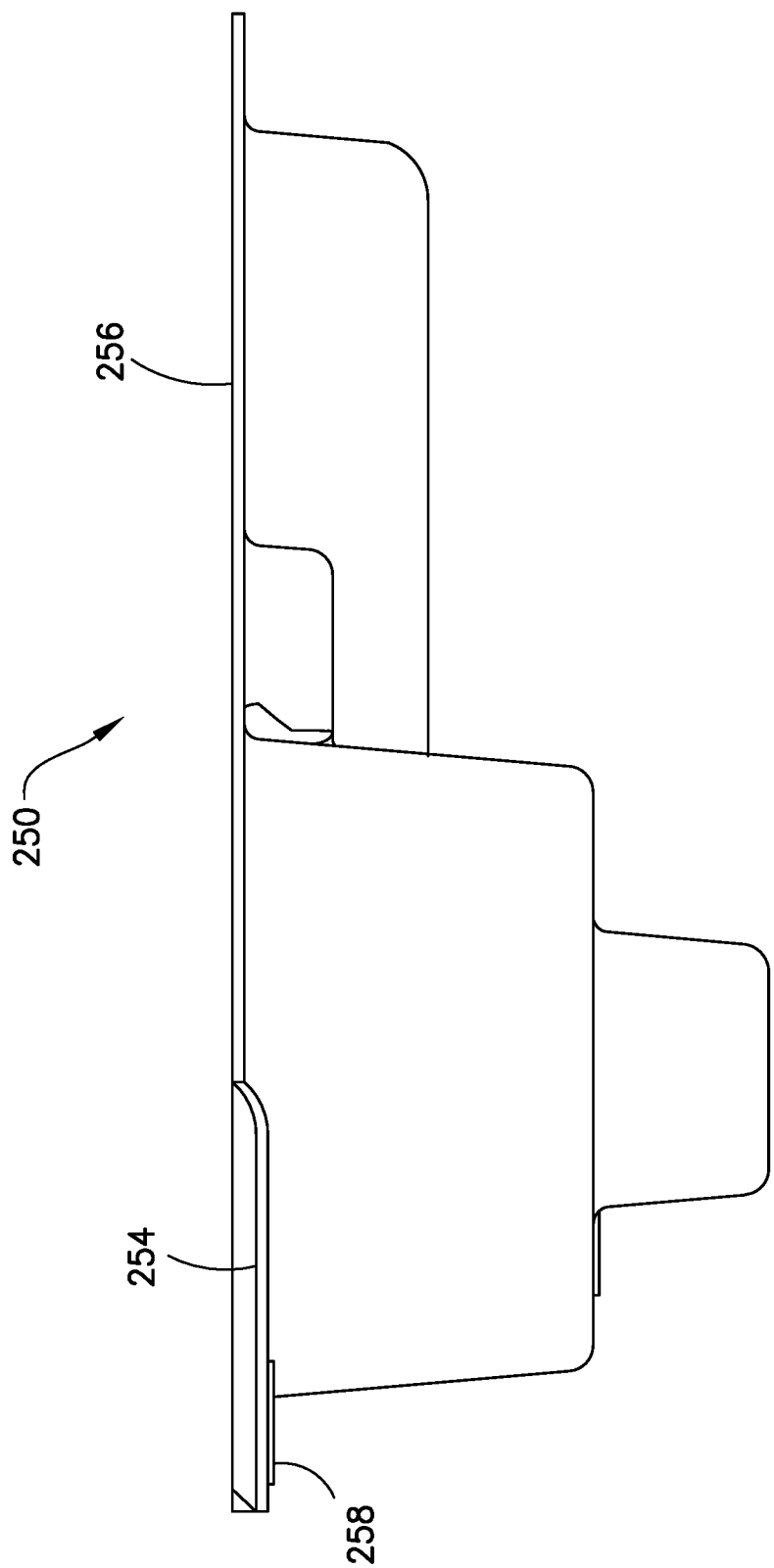
FIG. 20 is a right side view of the bottom portion of FIG. 18.

According to one embodiment, the recessed portion 254 has a marking 258. Preferably, the marking 258 is recessed below the recessed portion 254, as best shown in FIG. 20. In such an embodiment, even if the heat press adheres the barrier 114 to the recessed portion 254, because the marking is recessed below the recessed portion 254, the barrier will preferably not adhere to the marking 258, thereby allowing the user to peel back the lifting tab more easily at the location of the marking 258. Preferably, the marking 258 is an informational marking 258.

Figure 21:
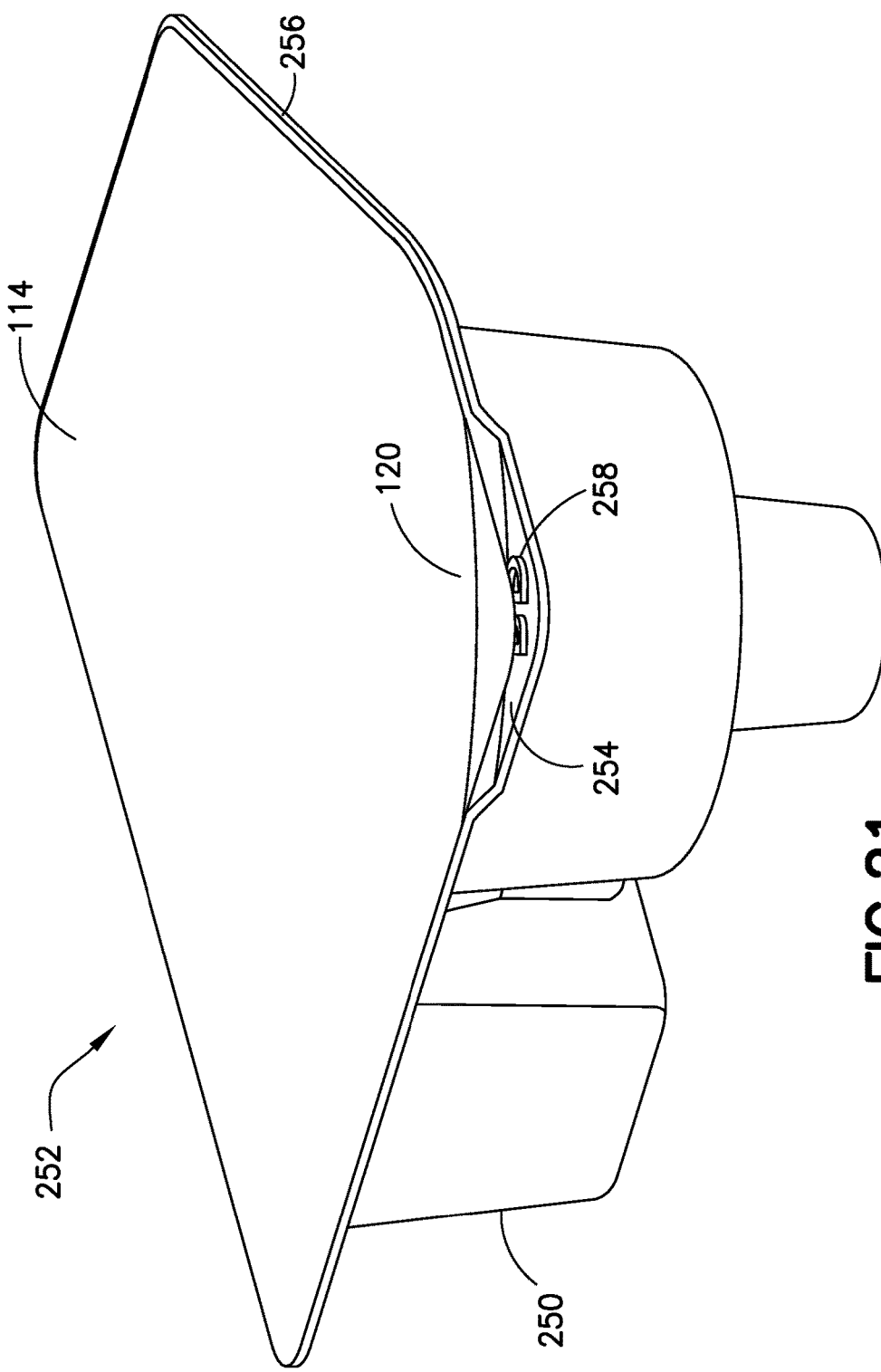
FIG. 21 is a perspective view of a package in accordance with an embodiment of the present invention, including the bottom portion of FIG. 18.

FIG. 21 is a perspective view of the package 252 illustrating the barrier adhered to the bottom portion 250 and sealing the package 252.

Figure 22:
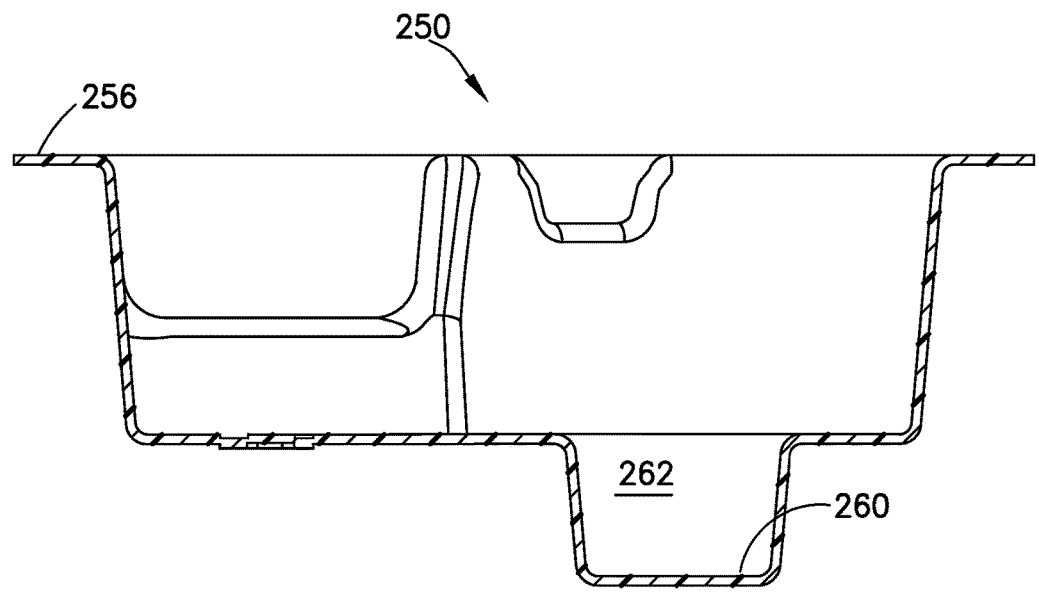
FIG. 22 is a cross-sectional view of the bottom portion of FIG. 18.
Figure 23:
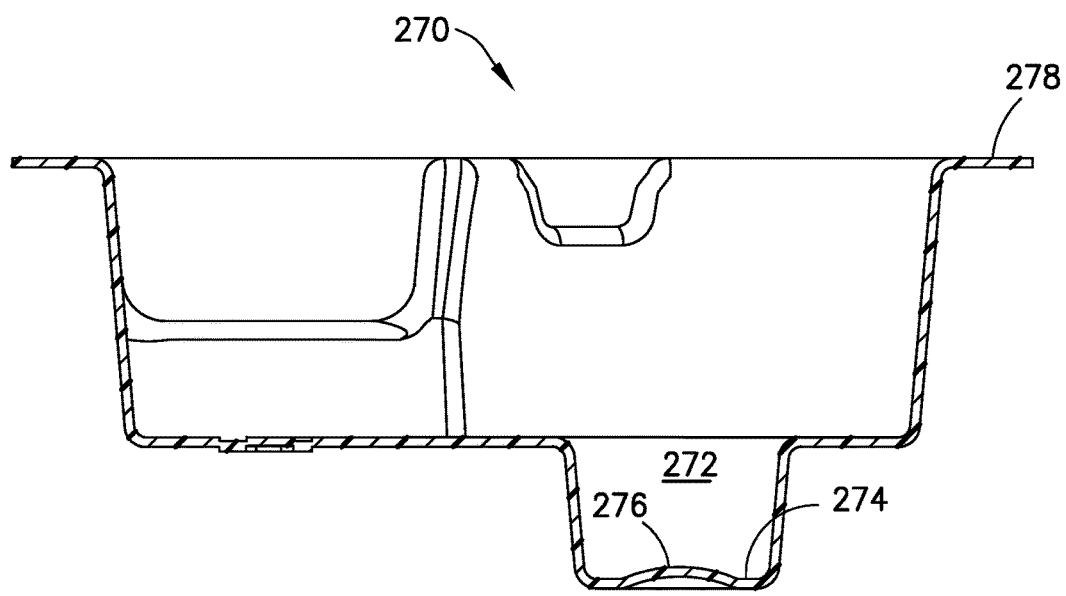
FIG. 23 is a cross-sectional view of a bottom portion in accordance with another embodiment of the present invention.
Figure 24:
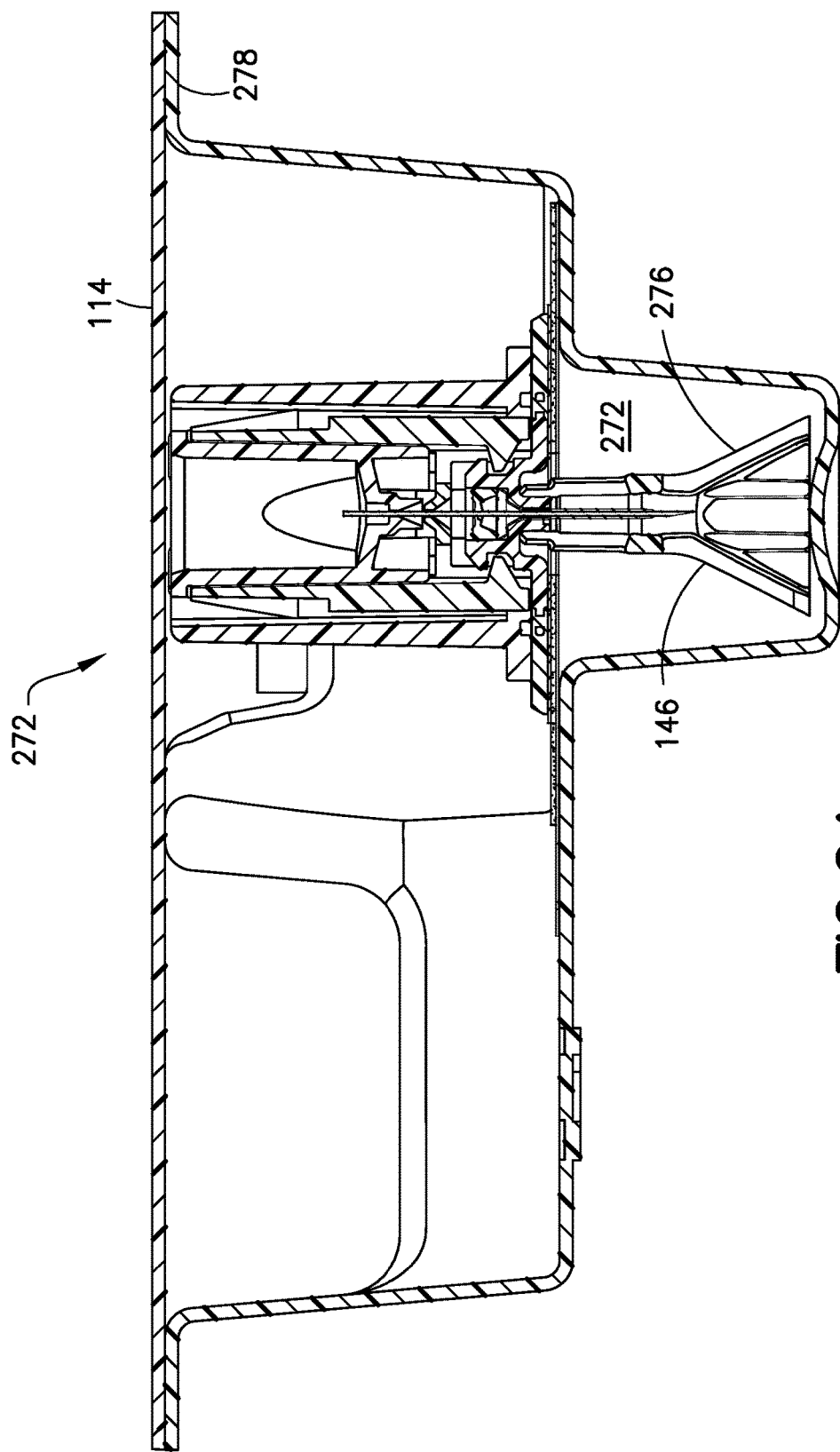
FIG. 24 is a cross-sectional view of a package including the bottom portion of FIG. 23 with a medical device disposed therein in accordance with an embodiment of the present invention.

FIG. 22 is a cross-sectional view of the bottom portion 250. A floor 260 of a guard recess portion 262 that receives the needle guard 146 is substantially flat. In contrast, as shown in FIG. 23, the bottom portion 270 has a guard recess portion 272 with a floor 274 having a mound or hump 276 protruding toward the flange 278 (and the barrier 114, as shown in FIG. 24). The mound or hump 276 engages a bottom of the needle guard 146 to help prevent displacement of the insertion set 126 relative to the bottom portion 270, as shown FIG. 24.

Figure 25:
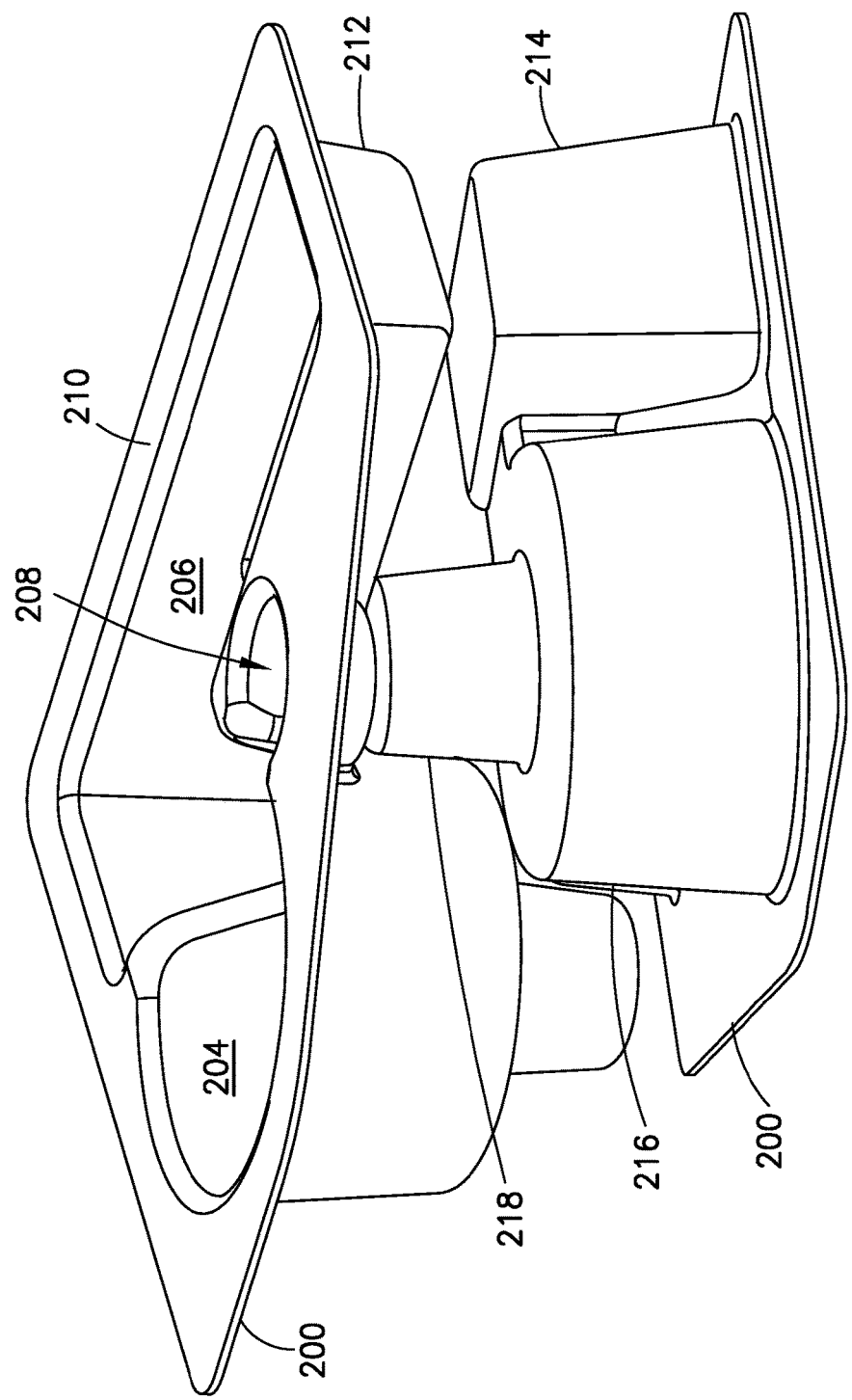
FIG. 25 is a perspective view of a nested pair of bottom portions of FIG. 13 in accordance with an embodiment of the present invention.
Figure 26:
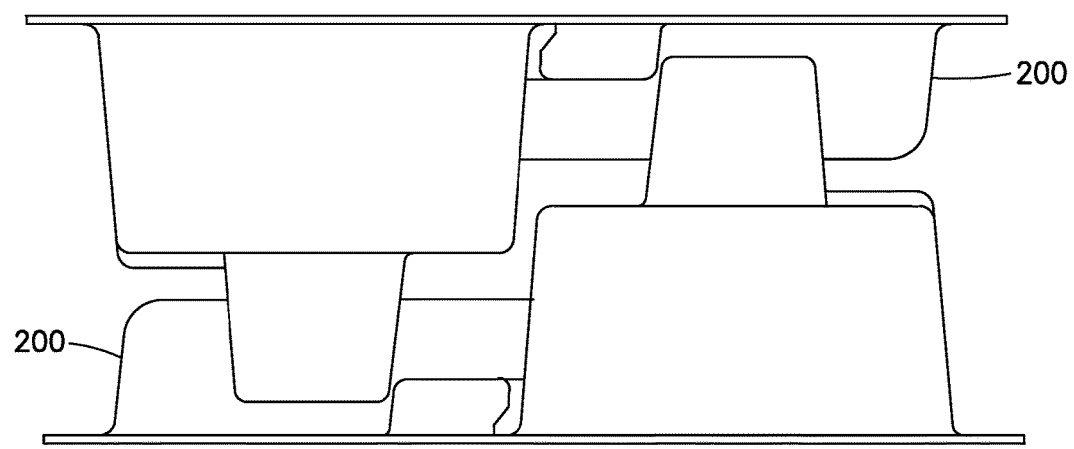
FIG. 26 is a left side view of the nested pair of bottom portions of FIG. 25.
Figure 27:
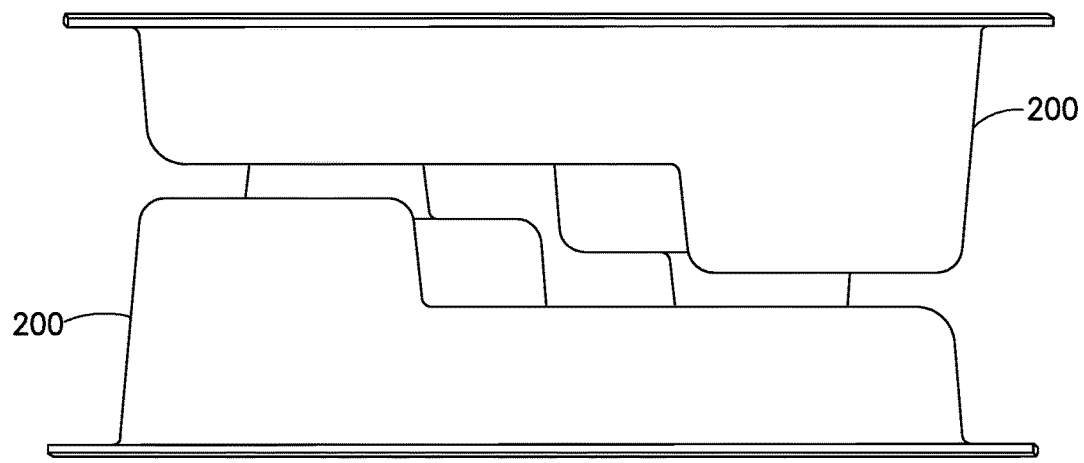
FIG. 27 is a right side view of the nested pair of bottom portions of FIG. 25.
Figure 28:
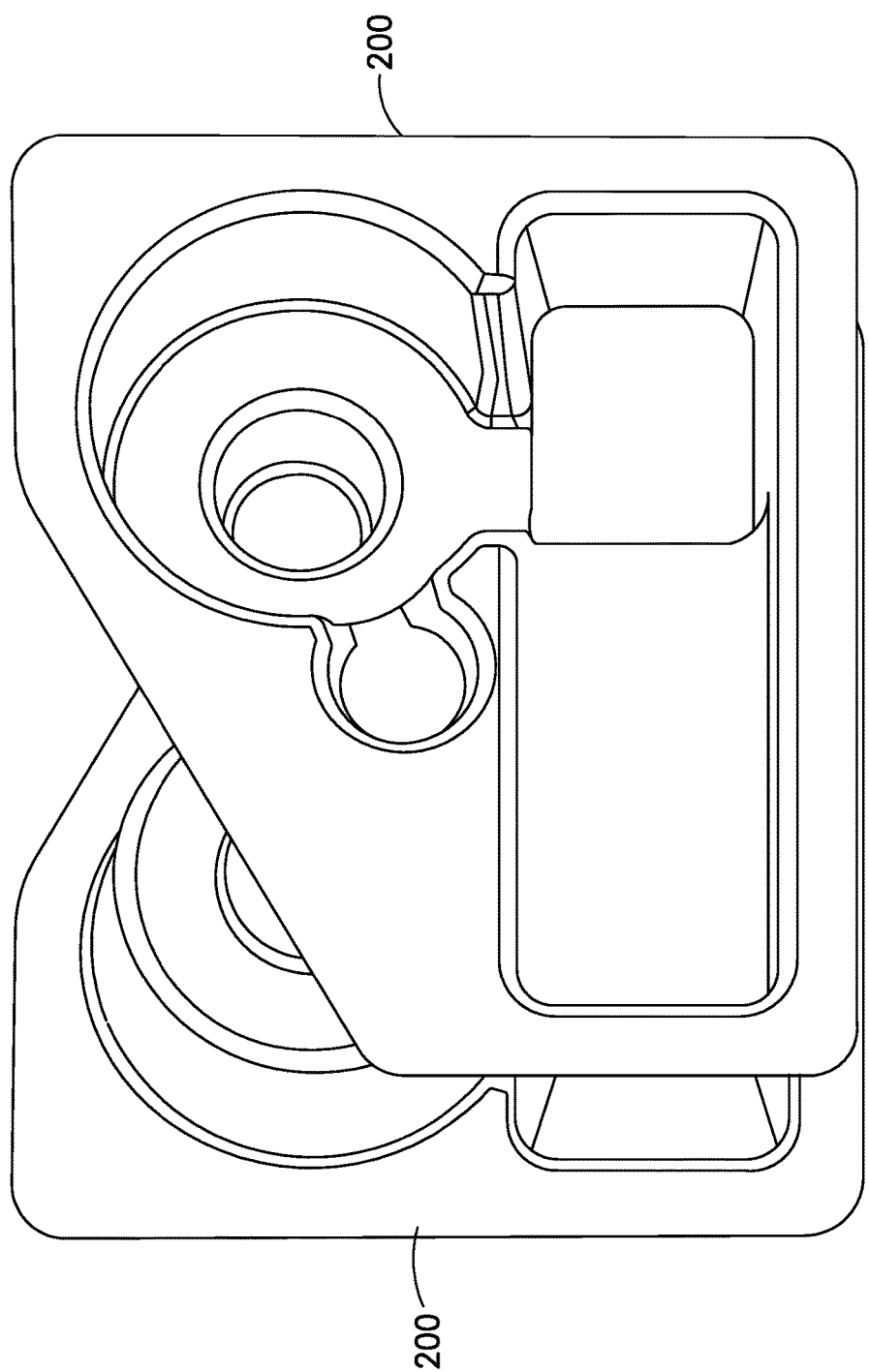
FIG. 28 is a perspective top view of the nested pair of bottom portions of FIG. 25.

FIG. 25 is a perspective view of a nested pair of bottom portions 200 (of FIG. 13) in accordance with an embodiment of the present invention. FIGS. 26 and 27 are respective left and right side views of the nested pair of bottom portions 200, and FIG. 28 is a perspective top view of the nested pair of bottom portions 200.

Although the barriers 114 are removed for clarity, FIGS. 25-28 illustrate that a pair of bottom portions 200 (and thus, packages 202) are contiguously nestable to minimize a packing volume thereof. In other words, when one package 202 is inverted relative to another package 202 and longitudinal axes (i.e., along the tubing set regions 206) are aligned, the packages 202 can fit or nest together to form a nested pair of packages. Put another way, nesting packages 202 inter-fit to save space, with or without interlocking. Interlocking can be defined as a resistance to separation in one or more directions, and can be achieved by friction and/or mechanical engagement.

Figure 29:
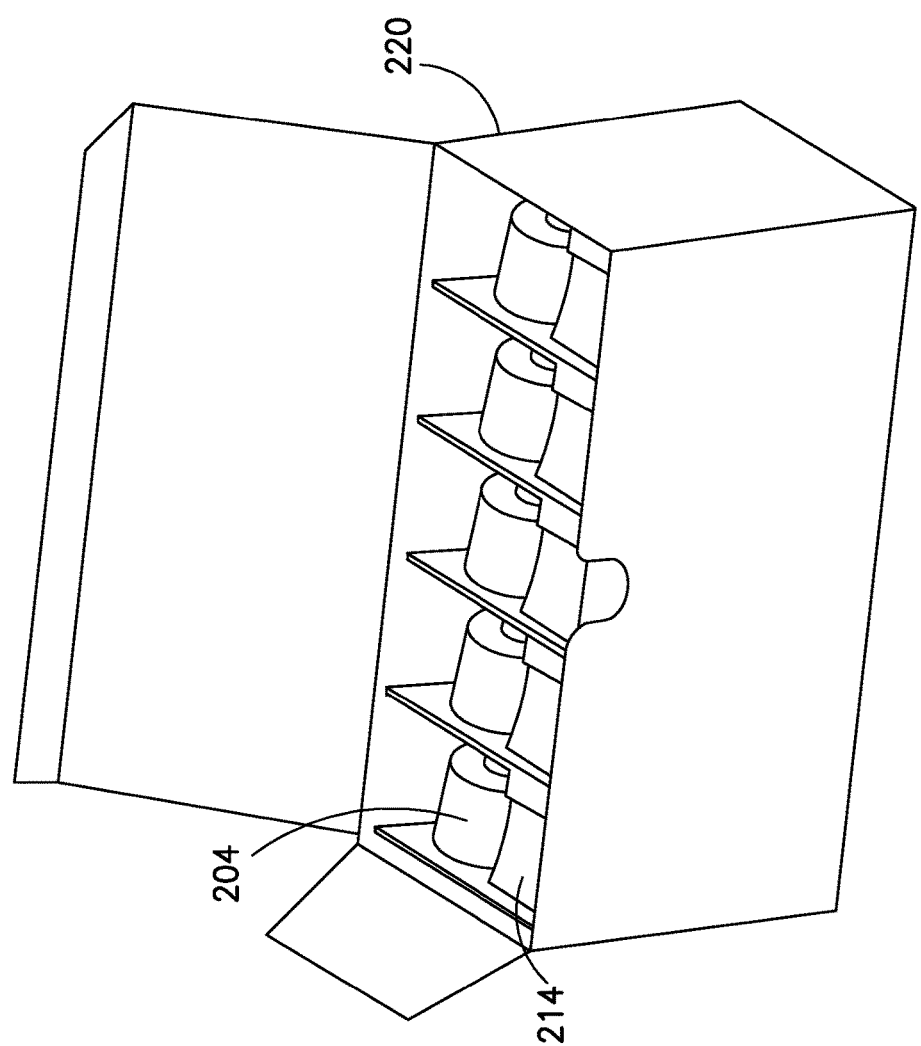
FIG. 29 illustrates a plurality of nested pairs of packages in a shelf carton in accordance with an embodiment of the present invention.

For example, as shown in FIG. 29, a barrier 114 of one of the packages of a nested pair can be positioned adjacent to a barrier 114 of one of the packages of another nested pair. When this is accomplished a plurality of nested pairs are placed in a shelf carton 220 with the longitudinal axes of the packages 202 being oriented substantially perpendicular to an opening of the shelf carton 220, the nested pairs form a top row and a bottom row. In FIG. 29, the top row is the row with the introducer assembly region 204 on top. In other words, the back row. Because the nested pairs of packages 202 preferably do not interlock, each of the packages 202 in the top row is freely removable from the shelf carton 220 through the opening.

According to one embodiment, the multi-component infusion set 122 can be used for about three days before being replaced. Thus, a user typically would use ten infusion sets 122 per month. Accordingly, a shelf carton 220 that contains ten infusion sets 122 would generally be a one-month supply. The shelf carton 220 shown in FIG. 29 is sized to contain ten infusion sets 122.

Figure 31:
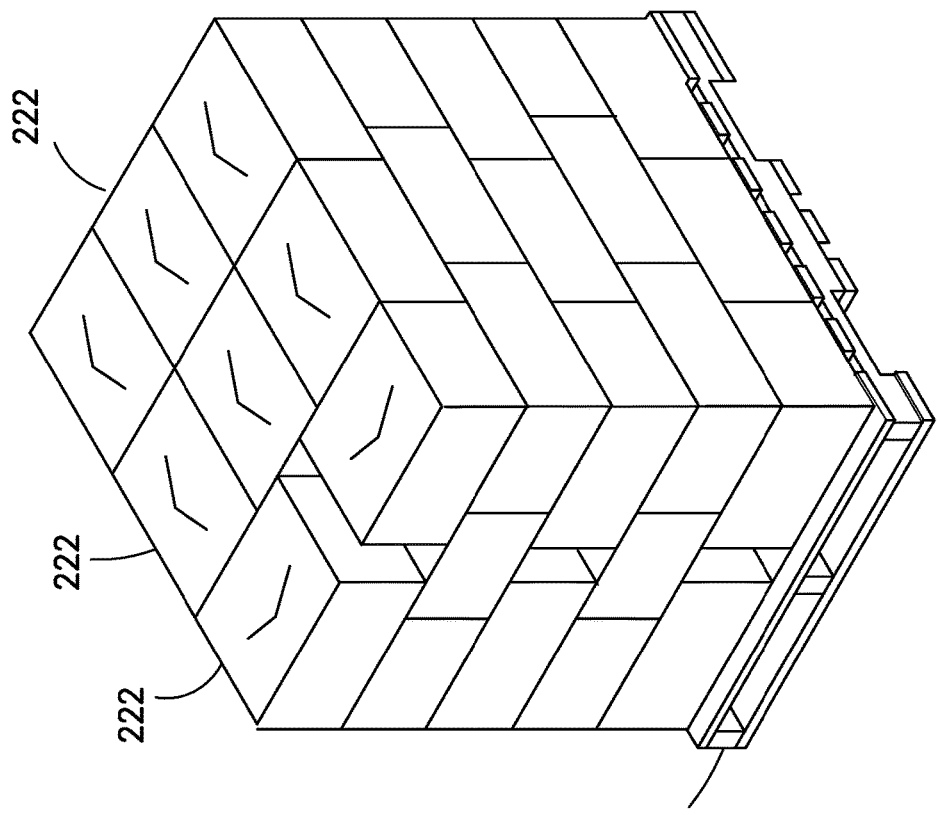
FIG. 31 illustrates a plurality of shipping cartons on a pallet in accordance with an embodiment of the present invention.
Figure 30:
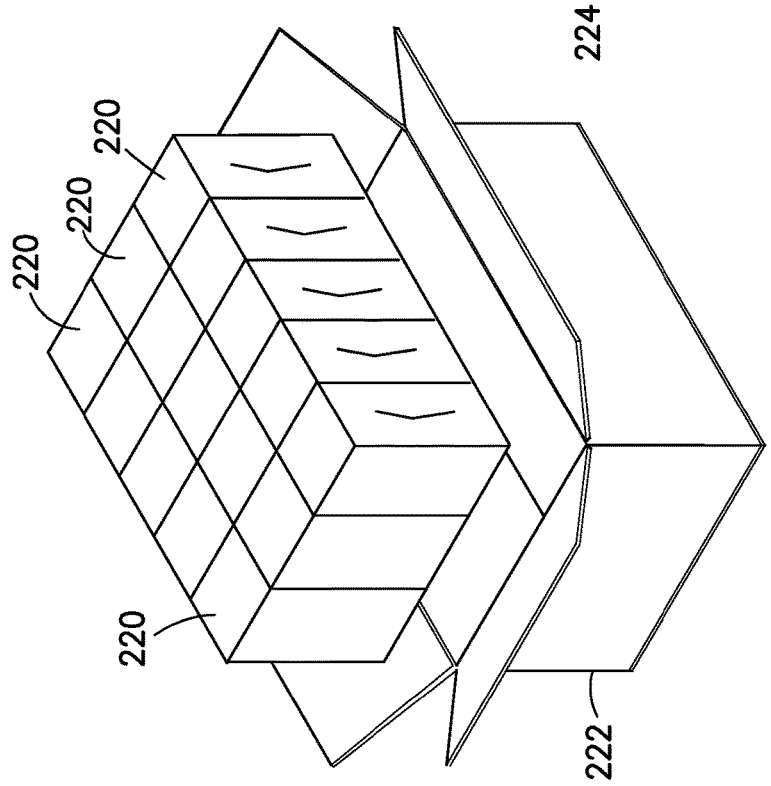
FIG. 30 illustrates a plurality of shelf cartons in a shipping carton in accordance with an embodiment of the present invention.

As shown in FIGS. 30 and 31, a shipping carton 222 can be sized to fit fifteen shelf cartons 220, and a standard pallet 224 can hold forty shipping cartons 222. Thus, a standard pallet 224 can hold 6,000 infusion sets 122 (10 infusion sets per shelf carton×15 shelf cartons per shipping carton×40 shipping cartons per pallet). As previously noted, the length of the cannula 140 and the needle guard 146 can vary according to desired cannula insertion depth. The guard recess portion 218 of the package 202 (for example, FIGS. 13-17) can be used for longer cannula and needle guard combinations, and therefore has a greater depth (distance from its floor to the flange 210) than the guard recess portion 262 of the package 250 (for example, FIGS. 18-24), which can be used for shorter cannula and needle guard combinations. FIGS. 25-31 and the calculation regarding infusion sets per pallet illustrate the package 202. If the package 250 with the shorter guard recess portion was employed, a standard pallet could hold approximately 7200 packages.

As previously disclosed, one or more raised or recessed formations, preferably in the form of informational markings, are provided on the flange to allow for easier barrier 114 removal by a user. Additionally, the platform 152 can be inserted into the bottom portion 150 to form a two-piece bottom housing for a medical device. Further, the bottom portion 200 allows the individual parts of the medical device 122 to be removed independently of one another. Each of the previously-described bottom portions 100, 150, and 200 can be formed using thermoforming. Moreover, by employing packages 202 as shown, the packages 202 can be nested, and thus, take up less space in and/or reduce the size of a shelf carton.

Although only a few embodiments of the present invention have been shown and described, the present invention is not limited to the described embodiments. Instead, it will be appreciated by those skilled in the art that changes may be made to these embodiments without departing from the principles and spirit of the invention, the scope of which is defined by the appended claims and their equivalents.

What is claimed is:

1. A pair of packaged multi-component medical devices, each packaged multi-component medical device comprising:
   a multi-component medical device comprising a plurality of components, each component comprising an individual element or a subassembly of individual elements; and
   a package in which the medical device is disposed, the package comprising:
      a bottom portion with cavities, each cavity providing individual access to a different component of the medical device, every component being removable from the package in any order without disturbing the remaining component or components, and each cavity forming a protrusion on a bottom surface of the bottom portion; and
      a barrier affixed to the bottom portion for sealing the package;
   wherein when the respective bottom portions of the pair are nested with two adjacent edges aligned, the protrusions interlock the packaged multi-component medical devices in a first direction but do not interlock the packaged multi-component medical devices in a second direction opposite to the first direction.

2. The combination according to claim 1, wherein the package comprises designated regions for each component.

3. The combination according to claim 2, wherein each designated region is recessed from an upper surface of the bottom portion.

4. The combination according to claim 1, wherein the components of the multi-component medical device comprise:
   an introducer assembly of an infusion set;
   an infusion tubing set;
   an infusion set base; and
   a sterile cap for covering an infusion set base during periods in which the tubing set is disconnected from the base; and
   wherein the package comprises designated regions for:
      the introducer assembly of the infusion set;
      the infusion tubing set; and
      the sterile cap.

5. The combination according to claim 4, wherein each designated region is recessed from an upper surface of the bottom portion.

6. The combination according to claim 5, wherein the region for the infusion tubing set comprises:
   a first region designated for the tubing; and
   a second region designated for a fluid connector for connecting the tubing to the base.

7. The combination according to claim 6, wherein the second region is recessed further from the upper surface of the bottom portion than the first region.

8. The combination according to claim 7, wherein:
   the region for the introducer assembly is contiguous with the region for the fluid connector and the region for the sterile cap; and
   the region for the tubing is contiguous with the region for the fluid connector.

9. The combination according to claim 4, wherein the region for the introducer assembly is contiguous with the region for the infusion tubing set and the region for the sterile cap.

10. The combination according to claim 4, wherein the regions for the infusion tubing set and the sterile cap are not contiguous.

11. The combination according to claim 4, wherein the region for the introducer assembly comprises:
   a first region recessed from an upper surface of the bottom portion; and
   a second region recessed from the first region;
   wherein the second region is recessed further from the upper surface of the bottom portion than the first region.

12. The combination according to claim 11, wherein a floor of the second region is substantially flat.

13. The combination according to claim 11, wherein a floor of the second region has a mound protruding toward the upper surface of the bottom portion.

14. A plurality of pairs according to claim 1, wherein when a barrier of a nested pair is positioned adjacent to a barrier of another nested pair in a shelf carton, and longitudinal axes of the packages are oriented substantially perpendicular to an opening of the shelf carton, the pairs form a top row and a bottom row; and
   each of the top row packages is freely removable from the shelf carton through the opening.

15. The combination according to claim 1, wherein the barrier is gas-permeable to allow gas sterilization of the medical device within the package.

16. The combination according to claim 1, wherein the barrier comprises paper with an adhesive polymer on one side.

17. The combination according to claim 1, wherein a portion of an upper surface of the bottom portion is recessed from an uppermost portion of the upper surface, to provide a flap in the barrier for ease of opening the package.

18. The combination according to claim 17, wherein, the recessed portion of the upper surface of the bottom package portion has a raised portion that is substantially flush with the uppermost portion of the upper surface.

19. The combination according to claim 17, wherein, the recessed portion has an informational marking that is one of:
   raised relative to the recessed portion to a level that is substantially flush with the uppermost portion of the upper surface; or
   recessed relative to the recessed portion.

20. The combination according to claim 1, wherein in each of the packaged multicomponent medical devices, one of the cavities comprises:
   a first region recessed from an upper surface of the bottom portion; and
   a second region, concentric with, central to, and recessed from the first region;
   wherein the second region is recessed further from the upper surface of the bottom portion than the first region.

21. A method of packaging a pair of multi-component medical devices, the multi-component devices each comprising a plurality of components, each component comprising an individual element or a subassembly of individual elements, the method comprising:
   for each multi-component medical device:
      forming a bottom portion with cavities, each cavity providing individual access to a different component of the medical device, and each cavity forming a protrusion on a bottom surface of the bottom portion; and
      inserting the components of the medical device into their respective cavities, thereby enabling a user to remove every component from the package in any order without disturbing the remaining component or components; and affixing a barrier to a rim of the bottom portion to seal the package; and nesting the respective bottom portions of the pair so that two adjacent edges of the respective bottom portions are aligned and the protrusions interlock the packaged multi-component medical devices in a first direction but do not interlock the packaged multi-component medical devices in a second direction opposite to the first direction.

22. The method according to claim 21, wherein the forming comprises thermoforming the bottom portion.

23. The method according to claim 21, wherein one of the cavities comprises:
    a first region recessed from an upper surface of the bottom portion; and
    a second region, concentric with, central to, and recessed from the first region, the second region being recessed further from the upper surface of the bottom portion than the first region.

24. A pair of packaged multi-component medical devices, each packaged multi-component medical device comprising:
    a multi-component medical device comprising a plurality of components, each component comprising an individual element or a subassembly of individual elements; and
    a package in which the medical device is disposed, the package comprising a bottom portion with cavities, each cavity providing individual access to a different component of the medical device, every component being removable from the package in any order without disturbing the remaining component or components, and each cavity forming a protrusion on a bottom surface of the bottom portion;
    wherein on each package:
        a first protrusion protrudes from a bottom surface of a flange a first distance;
        a second protrusion concentric with, central to, and protruding from the first protrusion protrudes from the bottom surface of the flange a second distance;
        a third protrusion protrudes from the bottom surface of the flange a third distance;
        a fourth protrusion, aligned with the third protrusion along a longitudinal axis of the package, protrudes from the bottom surface of the flange a fourth distance; and
        the second distance is greater than the third distance, which is greater than the first distance, which is greater than the fourth distance; and
    wherein when the packages are nested, the respective longitudinal axes are substantially parallel.

25. The combination according to claim 24, wherein the cavities that form the first through fourth protrusions are continuous.

26. A packaged multi-component medical device, comprising:
    a multi-component medical device comprising a plurality of components, each component comprising an individual element or a subassembly of individual elements; and
    a package in which the medical device is disposed, the package comprising a bottom portion with cavities, each cavity forming a protrusion on a bottom surface of the bottom portion;
    wherein:
        a first protrusion protrudes from a bottom surface of a flange a first distance;
        a second protrusion concentric with, central to, and protruding from the first protrusion protrudes from the bottom surface of the flange a second distance;
        a third protrusion protrudes from the bottom surface of the flange a third distance;
        a fourth protrusion, aligned with the third protrusion along a longitudinal axis of the package, protrudes from the bottom surface of the flange a fourth distance; and
        the second distance is greater than the third distance, which is greater than the first distance, which is greater than the fourth distance.

27. A method of forming packaging for a pair of multi-component medical devices, the multi-component devices each comprising a plurality of components, each component comprising an individual element or a subassembly of individual elements, the method comprising:
    forming a pair of bottom portions, each bottom portion having cavities for holding the components, each cavity forming a protrusion on a bottom surface of the respective bottom portion;
    wherein the respective bottom portions of the pair are nestable so that two adjacent edges of the respective bottom portions are aligned and the protrusions interlock the packaged multi-component medical devices in a first direction but do not interlock the packaged multi-component medical devices in a second direction opposite to the first direction.

* * * * *